(12) United States Patent
Zhao et al.

(10) Patent No.: US 11,298,095 B2
(45) Date of Patent: Apr. 12, 2022

(54) METHODS FOR X-RAY IMAGING OF A SUBJECT USING MULTIPLE-ENERGY DECOMPOSITION

(71) Applicant: XenseLab LLC, Irvine, CA (US)

(72) Inventors: Ying Zhao, Irvine, CA (US); YongSheng Chao, Storrs, CT (US)

(73) Assignee: XenseLab, LLC, Irvine, CA (US)

( * ) Notice: Subject to any disclaimer, the term of this patent is extended or adjusted under 35 U.S.C. 154(b) by 0 days.

(21) Appl. No.: 16/933,814

(22) Filed: Jul. 20, 2020

(65) Prior Publication Data

US 2021/0000436 A1 Jan. 7, 2021

Related U.S. Application Data

(63) Continuation of application No. PCT/US2019/014391, filed on Jan. 20, 2019.

(60) Provisional application No. 62/755,425, filed on Nov. 3, 2018, provisional application No. 62/745,369, filed on Oct. 14, 2018, provisional application No.

(Continued)

(51) Int. Cl.
*A61B 6/00* (2006.01)
*G01N 23/04* (2018.01)
*G01N 23/083* (2018.01)

(52) U.S. Cl.
CPC ............ *A61B 6/482* (2013.01); *A61B 6/4241* (2013.01); *A61B 6/5217* (2013.01); *A61B 6/5235* (2013.01); *A61B 6/5247* (2013.01); *A61B 6/5282* (2013.01); *A61B 6/582* (2013.01); *G01N 23/04* (2013.01); *G01N 23/083* (2013.01);

(Continued)

(58) Field of Classification Search
CPC ..... A61B 6/4216; A61B 6/4241; A61B 6/481; A61B 6/482; A61B 6/484; A61B 6/50; A61B 6/5217; A61B 6/5235; A61B 6/5247; A61B 6/5282; A61B 6/582; G01N 23/04; G01N 23/083; G01N 23/20091
See application file for complete search history.

(56) References Cited

U.S. PATENT DOCUMENTS 4,809,308 A  2/1989 Adams et al.
5,020,086 A  5/1991 Peugeot
(Continued)

FOREIGN PATENT DOCUMENTS

EP    3129957 B1    6/2019
WO   WO 2009/012453 A1   1/2009
(Continued)

OTHER PUBLICATIONS

Alvarez, Robert E. et al., "Energy-selective Reconstructions in X-ray Computerized Tomography," Physics in Medicine & Biology, vol. 21, No. 5, 1976, pp. 733-744.

(Continued)

*Primary Examiner* — Mark R Gaworecki
(74) *Attorney, Agent, or Firm* — Knobbe, Martens, Olson & Bear, LLP

(57) ABSTRACT

Methods for quantitatively separating x-ray images of a subject having three or more component materials into component images using spectral imaging or multiple-energy imaging with 2D radiographic hardware implemented with scatter removal methods. The multiple-energy system may be extended by implementing DRC multiple energy decomposition and K-edge subtraction imaging methods.

45 Claims, 19 Drawing Sheets

Related U.S. Application Data

62/713,554, filed on Aug. 2, 2018, provisional application No. 62/712,058, filed on Jul. 30, 2018, provisional application No. 62/711,522, filed on Jul. 28, 2018, provisional application No. 62/700,157, filed on Jul. 18, 2018, provisional application No. 62/692,675, filed on Jun. 30, 2018, provisional application No. 62/645,163, filed on Mar. 19, 2018, provisional application No. 62/628,351, filed on Feb. 9, 2018, provisional application No. 62/620,158, filed on Jan. 22, 2018.

(52) U.S. Cl.
CPC ............. *A61B 6/4216* (2013.01); *A61B 6/481* (2013.01); *A61B 6/484* (2013.01); *A61B 6/50* (2013.01)

(56) References Cited

U.S. PATENT DOCUMENTS

| | | | |
|---|---|---|---|
| 5,097,492 A | 3/1992 | Baker et al. | |
| 5,594,770 A | 1/1997 | Bowles et al. | |
| 5,771,269 A | 6/1998 | Chao | |
| 6,570,955 B1 | 5/2003 | Siffert et al. | |
| 6,816,564 B2 | 11/2004 | Charles, Jr. et al. | |
| 9,036,879 B2 | 5/2015 | Mendonca et al. | |
| 9,579,526 B2 | 2/2017 | Kunz et al. | |
| 2008/0013673 A1* | 1/2008 | Ruhmschopf | A61B 6/482 378/7 |
| 2009/0283682 A1* | 11/2009 | Star-Lack | A61B 6/482 250/363.1 |
| 2012/0148133 A1* | 6/2012 | Chen | G06T 11/008 382/131 |
| 2013/0307923 A1 | 11/2013 | Inglese et al. | |
| 2014/0133729 A1 | 5/2014 | Goshen | |
| 2014/0247919 A1 | 9/2014 | Zhang et al. | |
| 2015/0287193 A1 | 10/2015 | Kato et al. | |
| 2015/0359504 A1 | 12/2015 | Zhou et al. | |
| 2016/0095562 A1 | 4/2016 | Baturin et al. | |
| 2016/0213344 A1* | 7/2016 | Yi | A61B 6/5282 |
| 2018/0067061 A1 | 3/2018 | Butani et al. | |
| 2021/0137469 A1 | 5/2021 | Zhao | |
| 2021/0244374 A1 | 8/2021 | Zhao | |

FOREIGN PATENT DOCUMENTS

| | | |
|---|---|---|
| WO | WO 2011/156526 A2 | 12/2011 |
| WO | WO 2017/144474 A1 | 8/2017 |
| WO | WO 2017/205612 A1 | 11/2017 |
| WO | WO 2019/144065 A1 | 7/2019 |
| WO | WO 2019/183002 A2 | 9/2019 |
| WO | WO 2020/028422 A1 | 2/2020 |
| WO | WO 2021/108715 A1 | 6/2021 |

OTHER PUBLICATIONS

Gaudreault, David et al., "Comparative Study of Image Quality in Time-Correlated Single Photon Counting Computed Tomography," Journal of Latex Class Files, vol. 14, No. 8, Aug. 2015, in 7 pages.
Gordon, Richard, "A Tutorial on ART." IEEE Transactions on Nuclear Science, vol. NS-21, Jun. 1974, in 16 pages.
Mason, Jonathan H., "Quantative cone-beam CT reconstruction with polyenergetic scatter model fusion," Physics in Medicine & Biology, vol. 63, No. 22, Nov. 7, 2018.
Mccollough, Cynthia H. et al., Dual- and Multi-Energy CT: Principles, Technical Approaches, and Clinical Applications, Radiology, vol. 276, No. 3 Sep. 2015, pp. 637-653.
Sisniega, A. et al. "High-fidelity artifact correction for cone-beam CT imaging of the brain," Physics in Medicine & Biology, vol. 60, published Jan. 22, 2015, pp. 1415-1439.
International Search Report in corresponding International Patent Application No. PCT/US2019/014391, dated Apr. 29, 2020, in 2 pages.
Written Opinion in corresponding International Patent Application No. PCT/US2019/014391, dated Apr. 29, 2020, in 6 pages.
International Preliminary Report on Patentability in corresponding International Patent Application No. PCT/US2019/014391, dated Mar. 31, 2020, in 12 pages.
Inscoe, Christina R., "Stationary Digital Tomosynthesis: Implementation, Characterization, and Image Processing Techniques," The University of North Carolina at Chapel Hill, ProQuest Dissertations Publishing, 2018, in 171 pages.

* cited by examiner

Fig. 11 is a flow diagram of the method for further correction or calibration of the fat tissue and lean tissue images.

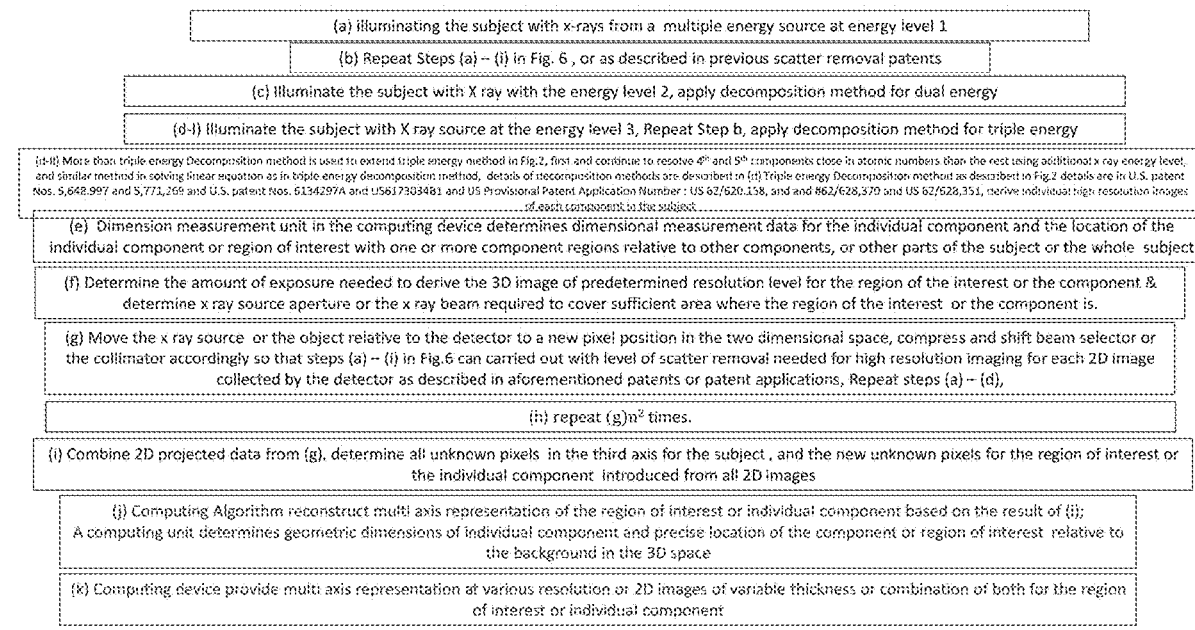
Fig. 12 Multiple Energy High Resolution 3D

2D Functional Imaging

I.
*Dual or Multiple Energy*

For each position x ray source emitting from,
1) dual or multiple energy method is used to separate components in the imaged object
2) Density measurement for separated components in the imaged object
3) Dynamic movement of components or region of interest or imaged object or tracking of location of a foreign object (s) in 2D

Fig. 13

II
*Interferometer*
a. interference image of primary x ray absorption imaging
b. Dark Field Imaging ( Scattered X ray) c. Phase Contrast Imaging Tablou interferometer
Mem based
Crystal based Multiple emitting points in one x ray source
Pixelated x ray source

III
*Energy Sensitive Photon Counting Detector*

*Single Detector used with time of flight x ray source*

*Or Energy Sensitive Photon Counting Detector may be the front or rear or both detectors in the dual detector assembly.*

IV
*1D -3D Mapping Technique for measure thickness and composition of components and region of interest* a. Densitometry and component separation and characteristics by putting a 3D microstructure in between the imaging object and the front detector and calibration method b. Densitometry and component separation and characteristics by putting a physical 3D microstructure in between the front and back detector c. 3D microstructured generated by modulation, for example acoustic modulator.

3D Functional Imaging

| I. | II. | III. a | III.b | IV |
|---|---|---|---|---|
| *Single, Dual or Multiple Energy 3 D image* | *Interferometer*<br>*a. interference image of primary x ray absorption imaging*<br>*b. Dark Field Imaging (Scattered X ray) c. Phase Contrast Imaging* | *Energy Sensitive Photon Counting Detector Decomposition of Material & Components* | *Single Energy 3D X-rayTomography Material Decomposition* | *3D Mapping Technique for measure thickness and composition of components and region of interest* |
| For each position x ray source emitting from,<br>1) Reconstruction of Images at single, dual or multiple energy levels<br>2) Density measurement for separated components in the imaged object<br>3) Dynamic movement of components or region of interest or imaged object or tracking of location of suspended component or a foreign object (s) in 3D<br>4) Kinetic studies of component, tissue or molecule or cell interaction | Reconstruct 3D representation for each type of image | Reconstruct 3D representation for each type of image | | a. Densitometry and component separation and characteristics by putting a 3D microstructure in between the imaging object and the front detector and calibration method<br><br>b. Densitometry and component separation and characterization by putting a physical 3D microstructure in between the front and back detector<br>c. 3D microstructured generated by modulation, for example acoustic modulator.<br><br>Reconstruct 3D representation for each type of image and tracking of a suspended component, dynamic movement of an adherent component Kinetic studies of component, or tissue or molecule or cell interaction |

Fig. 14

Fig 63 (Pre-a) Calibration

Fig 63 (a) & (b) is replace with Fig. 67 (a) –(d)

(a) illuminating the subject with x-rays from a dual energy x ray source at the high energy level H (b) as described in previous scatter and primary x ray patents in Fig 66 or as examples listed in Fig 53

(c) Illuminate the subject with X ray with the low energy level L, Repeat Step (b)

(d) Dual energy images are decomposed as described in Patent Application #, derive individual high resolution images of each component in the subject, (d) details are in U.S. patent Nos. 5,648,997 and 5,771,269, and U.S. patent Nos. 6134297A and US617303491. US Provisional Patent Application Number : US 62/620,158, and and #62/628,370 and US 62/628,351, derive individual high resolution images of each component in the subject (e) Fig 63 (c) - (g)

(f) Computing device provide multi axis representation at various resolution or 2D images combined with multiple dimension representation of both or functional images such as separated material or component or tissue and densitometry information for the region of interest, components and or the subject Fig. 15 Dual Energy High Resolution 3D Fig 63 (Pre-a) Calibration Fig 63 (a) & (b) is replaced with Fig 68 (a) –(f)

(a) illuminating the subject with x-rays from a triple energy x ray source at the high energy level H (b) as described in previous scatter and primary x ray patents in Fig 66 or as examples listed in Fig 53

(c) Illuminate the subject with X ray with the low energy level L, Repeat Step b (d) Illuminate the subject with X ray with the middle energy level M, Repeat Step b (e) Triple energy Decomposition method as described in Fig.2 details are in U.S. patent Nos. 5,648,997 and 5,771,269 and U.S. patent Nos. 6134297A and US6173034B1 and US Provisional Patent Application Number : US 62/620.158, and and #62/628,370 and US 62/628,351, derive individual high resolution images of each component in the subject (f) X ray source or x ray emitting position shifts or the subject moves, to a second position in a plane parallel to the detector. The shift distance between x ray emitting positions is set so that each picture contains projected images of the region of interest whose location differ from the previous one by extending the outer rim of detected image for region of interest by exactly one linear pixel line on the detector, and along the axis of shifting direction, Repeat (a) –(d) Functional Imaging Step.

(g) Determine geometry or dimension of region of interest in the subject or the subject ; if such information is predetermined and stored in the computing device, skip this step.

(h) Fig 63 (c) - (g)

(i) Computing device provide multi axis representation at various resolution or 2D images combined with multiple dimension representation of both or functional images such as separated material or component or tissue and densitometry information for the region of interest, components and or the subject Fig. 16 One embodiment of 3D Functional Imaging: Triple Energy, High Resolution, 3D Fig 63 (Pre-a) Calibration Fig 63 (a) & (b) is replaced with Fig 68 (a) –(f)

(a) illuminating the subject with x-rays from a triple energy x ray source at the high energy level H (b) as described in previous scatter and primary x ray patents in Fig 66 or as examples listed in Fig 53

(c) Illuminate the subject with X ray with the low energy level L, Repeat Step b (d) Illuminate the subject with X ray with the middle energy level M1, Repeat Step b ; Illuminate the Subject with X ray with a different middle energy level M2, Repeat Step b (e) Extend Triple energy Decomposition method to four or more energy levels, as described in Fig.54, details are in US Provisional Patent Application Number : US 62/620.158, and and #62/628,370 and US 62/628,351, derive individual high resolution images of each component in the subject; Or alternatively, use an energy sensitive photon counting detector as the front or back detector in Fig. 66. or just a single stand alone detector, separate tissue images or densitometry information is automatically detected.

(f) X ray source or x ray emitting position shifts or the subject moves, to a second position in a plane parallel to the detector. The shift distance between x ray emitting positions is set so that each picture contains projected images of the region of interest whose location differ from the previous one by extending the outer rim of detected image for region of interest by exactly one linear pixel line on the detector, and along the axis of shifting direction, Repeat (a) –(d) Functional Imaging Step.

(g) Determine geometry or dimension of region of interest in the subject or the subject ; if such information is predetermined and stored in the computing device, skip this step.

(h) Fig 63 (c) - (g)

(i) Computing device provide multi axis representation at various resolution or 2D images combined with multiple dimension representation of both or functional images such as separated material or component or tissue and densitometry information for the region of interest, components and or the subject Fig. 17 One embodiment of Functional Imaging: Multiple Energy High Resolution 3D

METHODS FOR X-RAY IMAGING OF A SUBJECT USING MULTIPLE-ENERGY DECOMPOSITION

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application claims the benefit under 35 U.S.C. § 120 and 35 U.S.C. § 365(c) as a continuation of International Application No. PCT/US2019/014391, designating the United States, with an international filing date of Jan. 20, 2019, titled "METHODS FOR X-RAY IMAGING OF A SUBJECT USING MULTIPLE-ENERGY DECOMPOSITION," which claims the benefit of U.S. Patent Application No. 62/620,158, filed Jan. 22, 2018; U.S. Patent Application No. 62/628,351, filed Feb. 9, 2018; U.S. Patent Application No. 62/645,163, filed Mar. 19, 2018; U.S. Patent Application No. 62/692,675, filed Jun. 30, 2018; U.S. Patent Application No. 62/700,157, filed Jul. 18, 2018; U.S. Patent Application No. 62/711,522, filed Jul. 28, 2018; U.S. Patent Application No. 62/712,058, filed Jul. 30, 2018; U.S. Patent Application No. 62/713,554, filed Aug. 2, 2018; U.S. Patent Application No. 62/745,369, filed Oct. 14, 2018; and U.S. Patent Application No. 62/755,425, filed Nov. 3, 2018. The entirety of each of the aforementioned applications is incorporated by reference herein.

TECHNICAL FIELD

The present invention relates generally to digital x-ray imaging and, more particularly, to methods and apparatuses for enhancing the functional imaging value of x-ray images for diagnosis, testing, image guidance, analysis and material identification & characterization, real time tracking, chronological monitoring, localization of each component in a subject comprised of multiple components.

BACKGROUND ART

Large-format, two-dimensional, semiconductor digital x-ray detector arrays have been widely adopted for medical imaging and nondestructive testing. Generally, all of the image information is contained in a single projected image, where internal details of the subject are masked by overlapping components. Where multiple-energy x-rays have been used, the image data is for visual illustration and analysis generally as quantitative analysis of the measured data is not available due to the lack of accuracy required for most applications.

Generally, a human body component, for example, the chest, is comprised of several major substances, the soft tissue, comprising lean tissue and the fat tissue, blood vessels, heart, mostly lean tissue, lung, mostly lean tissue with air cavities, bone, and in some cases, microcalcification deposits, and other soft tissue structures. Each pixel of such a single image contains a mixture of all tissues, plus a random scatter component. The amount of the contribution from each component is not known in current digital chest imaging systems where 2D digital x-ray detectors are used.

It is well-established that the role of the random scatter signal in an x-ray imaging is interference and distortion. The scatter blurs the image, reduces the image contrast, and degrades the image quality. The contribution of scatter in chest imaging is 20% or more.

For example, in the screening of lung cancer, identification and characterization of both microcalcification and non-calcification nodules are important. Because of the inability to separate the basic component in chest imaging, the capability of the current x-ray imaging using 2D detectors for lung cancer diagnosis is limited compared to computation tomography.

In many applications, such as human body imaging, spectral imaging utilizing 2D flat panel detectors is not accurate nor clinically relevant compared to spectral imaging of CT imaging, which is a quantitative method, due to the presence of scatter.

The present invention is based, in part, on the apparatus and methods disclosed in U.S. Pat. Nos. 5,648,997, 5,771, 269, and 6,052,433 (the Chao disclosures).

DISCLOSURE OF THE INVENTION

The present invention relates generally to digital x-ray imaging and, more particularly, to a method of digital imaging of region of interest, for example, in a human body or in a non-destructive testing environment. The present invention uses multiple energy apparatuses and methods for separating an x-ray image for multiple components in the region of interest into component images from the same projected 2D image path, each representing at least one single physical substance.

The present invention also relates to using quantitative analysis methods to minimize radiation required in determining and separating component images. For example, a spectral imaging system, such as a three-energy system, may separate four or more different components, each with a unique signature in terms of physical substance, or a spatial location compared to the rest or both. Similarly, a four-energy system may separate, five or more different components.

It is one aspect of the present invention to include A-space methods or similar methods which uses a broad spectrum x-ray beams or multiple monochromatic x ray beams spanning a broad x ray spectrum and measures the transmitted spectrum with photon counting detectors with pulse height analysis or energy sensitive detectors.

The present invention relates to using quantitative analysis methods to determine and separate components, whether internal or foreign to the region of interest, from the background based on their unique atomic z or molecular composition and microstructure or densities or spatial characteristics including dimensions, shape, pattern, or combination of two or more aforementioned characteristics.

Objects of the present invention will become apparent in light of the following drawings and detailed description of the invention.

BRIEF DESCRIPTION OF THE DRAWINGS

For a fuller understanding of the nature and object of the present invention, reference is made to the accompanying drawings, wherein:

FIG. 12 illustrates methods of obtaining multiple energy high resolution in 3D.

FIG. 13 illustrates 2D functional imaging features.

FIG. 14 illustrates 3D functional imaging features.

FIG. 15 illustrates methods of obtaining dual energy high resolution in 3D.

FIG. 16 illustrates one embodiment of 3D functional imaging using triple energy.

FIG. 17 illustrates one embodiment of 3D functional imaging using multiple energy.

BEST MODES FOR CARRYING OUT THE INVENTION

The present invention provides methods for quantitatively separating an x-ray image of a subject, such as a chest x-ray image, into a number of component images: a scatter image, a lung image, bone image, blood vessel image, other soft tissue image, and microcalcification image. The present invention provides methods for separating components in a region of interest in an NDT application.

In some embodiments, the present invention employs dual-energy x-ray imaging system hardware configurations described in U.S. Pat. Nos. 5,648,997, 5,771,269, and 6,134,297 (the Chao disclosures).

Apparatus

Primary X-Ray and Scatter Separation Hardware Configurations

Figure 1:
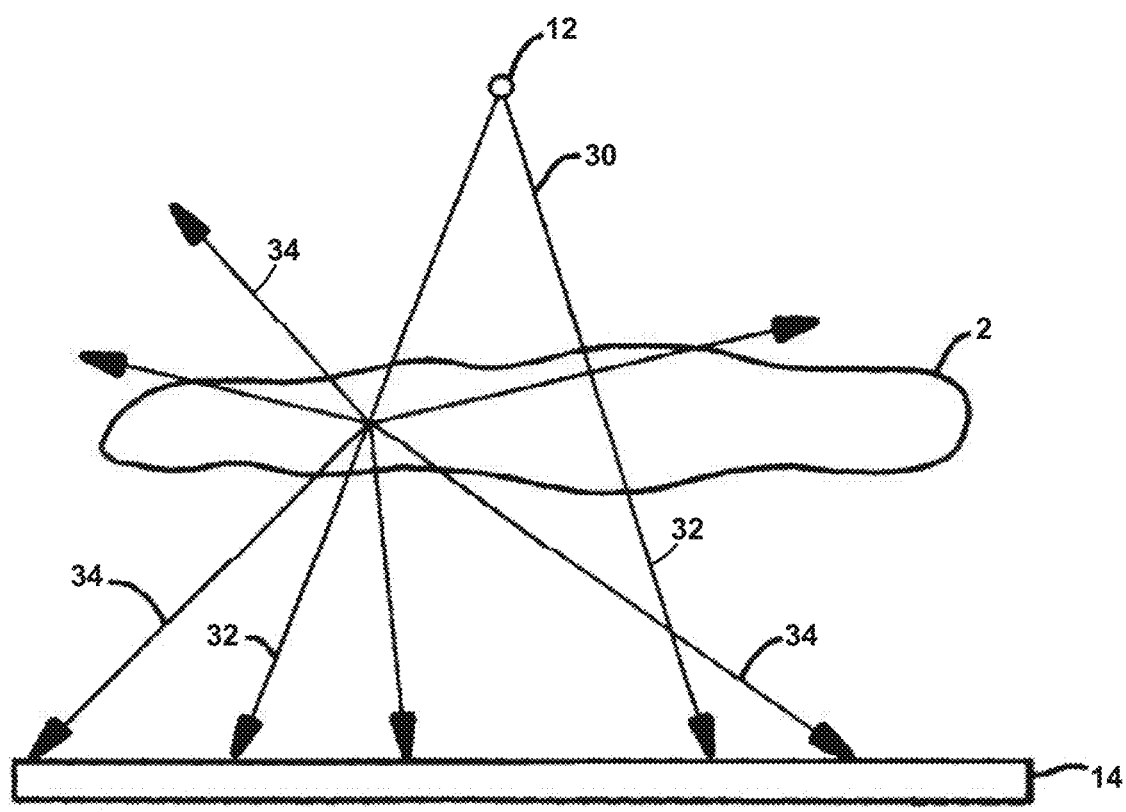
FIG. 1 is a schematic diagram of a basic hardware system of the present invention.

Referring to FIG. 1, when x-rays 30 from an x-ray source 12 impact on a subject 2, a portion of the x-rays 30 passes through the subject 2 directly to the detector assembly 14 without a change in the direction of propagation. These are primary x-rays 32 and convey true information about the attenuation properties of subject 2. The remainder of the x-rays 30 are randomly scattered as a result of interactions with the material of the subject 2. These are called scatter 34 and distort the true information.

The present invention employs one or more configurations of separating primary x-rays and scatter. Typically, these methods are used to remove scatter from an image. Consequently, these methods are also referred to as scatter removal methods. However, both primary x-ray and scatter images can be useful in representing true information about the subject.

One configuration for the removal of scatter does not really remove scatter. The detector assembly 14 is a single 2D detector 20 that receives both primary x-rays 32 and scatter 34. The method merely presumes that scatter 34 is present but in a sufficiently small amount that qualitatively correct, yet quantitatively inaccurate, imaging results can still be obtained under certain circumstances. To what extent the amount of scatter 34 is acceptable is case-dependent and must be determined by a case-specific analysis.

Another method is the separation of primary x-rays and scatter in the time domain. It employs the characteristic that primary x-rays 32 travel in a straight line from the source 12 to the detector assembly 14, taking the least amount of time in transit. Because scatter 34 does not travel in a straight line from the source 12 to the detector assembly 14, it takes a longer to reach the detector assembly 14. Consequently, x-rays reach any given detector cell 28 continuously over a period of time, where only the first x-rays are the primary x-rays. All others are scatter.

In an example of this configuration, the source 12 is capable of generating x-rays in extremely short pulses, for example, on the order of a picosecond in duration, and the detector assembly 14 is a 2D detector capable of extremely fast image capture, on the order of a picosecond. The captured image includes the primary x-rays 32 and the scatter 34 that reaches the detector during the capture time window. If the capture window is short enough, the amount of scatter 34 in the captured image is minimized. As the capture window becomes shorter, scatter 34 becomes a smaller component of the captured image.

Figure 2:
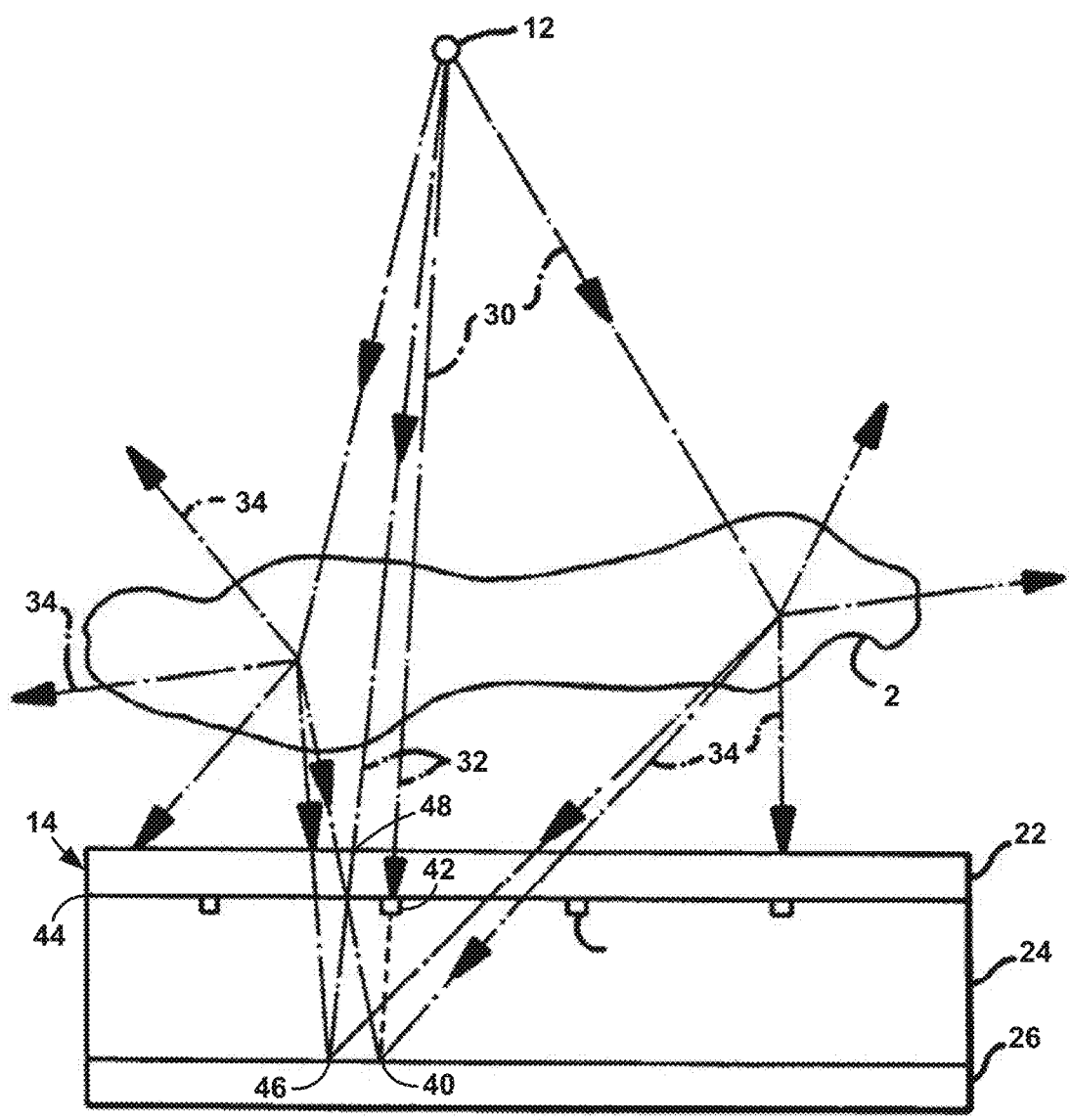
FIG. 2 is a schematic diagram of a first configuration of the hardware system employed by the present invention.

Another configuration of primary x-ray and scatter separation is described in U.S. Pat. No. 6,134,297. The detector assembly 14, shown in FIG. 2, is a three-layer structure of a front 2D detector 22 closest to the source 12, a 2D beam selector 24, and a rear 2D detector 26. The primary x-rays 32 and scatter 34 reach and pass through the front detector 22. The beam selector 24 allows only scatter 34 through to selected locations 40 of the rear detector 26.

An embodiment of the beam selector 24 is an array of cylinders 42 composed of x-ray-absorbent material and supported by a thin plastic sheet 44 having negligible x-ray absorption. The cylinders 42 are fabricated such that their axes are aligned with the direction of the travel of the primary x-rays 32, which means that the cylinders 42 are not parallel to each other, but are radial to the x-ray source 12. As a result, the cylinders 42, within their cross-sectional areas, block all x-rays coming directly from the x-ray source 12. Thus, each cylinder 42 produces a "shadowed" location 40 on the rear x-ray detector 26 where the strength of the primary x-rays 32 is essentially zero, while the strength of the scatter 34 is essentially unaffected.

Because the cylinders 42 have a finite size, a small portion of scatter 34 will be blocked from the shadowed locations 40. However, as long as the cylinders 42 are small, this blocked scatter 34 can be negligibly small. If the cylinders 42 are too large or are too close together, too much scatter 34 would be blocked from the rest of the rear detector 26.

The more cylinders 42 there are in the beam selector 24, the greater the accuracy of the measurement at the rear detector 26.

The material of the cylinder 42 must ensure that substantially all primary x-rays 32 are absorbed and, further, that it does not produce any secondary x-ray emission or cause any additional scattering. To meet these requirements, chemical elements with a medium atomic number Z are preferred, for example, materials with Z between 20 and 34. The cylinders 42 can also have a multilayer structure, with a high-Z material in the core and a medium-Z material outside. The high-Z material absorbs x-rays most efficiently and any secondary x-ray emissions from the core material are efficiently absorbed by the outside layer without inducing further secondary emissions.

The thickness or the height of the cylinders 42 is dependent upon the x-ray energy, where higher-energy x-rays require thicker cylinders. In lower-energy x-ray imaging, for example, in soft tissue imaging, the cylinders 42 can be thin disks.

The above-described detector assembly 14 is used to remove scatter 34 from the image as follows. A low-resolution scatter-only rear image is read from the shadowed locations 40 of the rear detector 26. A low-resolution composite (combined primary x-rays 32 and scatter 34) rear image is read from chosen locations 46 of the rear detector 26 that receive both primary x-rays 32 and scatter 34, that uniformly cover the entire image plane of the rear detector 26, and are close to the shadowed locations 40. The scatter-only image is extended to the chosen locations 46 by interpolation. The interpolation does not cause significant error because of the physical nature of the scatter 34. As long as there are a sufficiently large number of data points, the error incurred due to interpolation is negligible in comparison with other error sources, such as statistical fluctuations of x-ray photon numbers.

The scatter-only interpolated rear image is subtracted from the low-resolution composite rear image to produce a low-resolution primary x-ray rear image at the chosen locations 46. A low-resolution primary x-ray front image is calculated from the front detector locations 48 aligned with the x-ray source 12 and the rear detector chosen locations 46. A low-resolution scatter front image is determined by subtracting the low-resolution primary x-ray rear image from the low-resolution composite front image. A high-resolution scatter front image is calculated by interpolating the low-resolution scatter front image. The high-resolution scatter front image is subtracted from the high-resolution composite front image to produce a high-resolution primary x-ray image.

Figure 3:
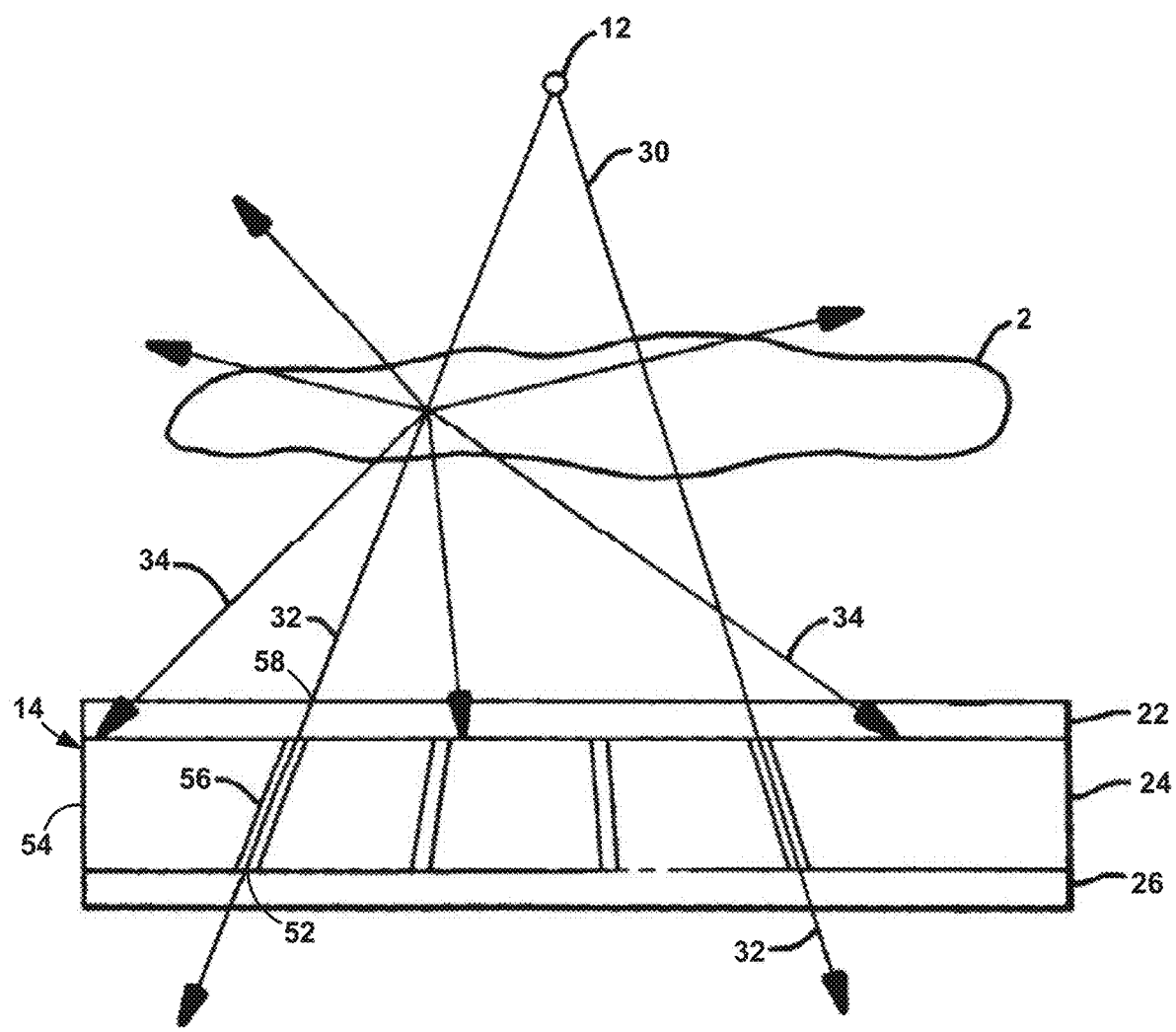
FIG. 3 is a schematic diagram of a second configuration of the hardware system employed by the present invention.

Another configuration of primary x-ray and scatter separation is described in detail in U.S. Pat. Nos. 5,648,997 and 5,771,269. The detector assembly 14, shown in FIG. 3, is a three-layer structure of a front 2D detector 22 closest to the source 12, a 2D beam selector 24, and a rear 2D detector 26. The combination of primary x-rays 32 and scatter 34 reach and pass through the front detector 22. The beam selector 24 allows only primary x-rays 32 through to selected locations 52 of the rear detector 26.

In the simplest configuration, the beam selector 24 is a sheet 54 of x-ray-absorbent material having a large number of straight through holes 56. The holes 56 are fabricated such that their axes are aligned with the travel direction of the primary x-rays 32, which means that, because the x-rays are emitted from essentially a point source, the holes 56 are not parallel to each other, but are radially aligned with the x-ray source 12.

Because of this alignment, the holes 56 permit all x-rays traveling along the axes of the holes 56 to pass through, while almost all x-rays traveling in directions deviating slightly from the hole axes are completely absorbed by the bulk material of the beam selector sheet 54. Thus, only the primary x-rays 32 reach the rear detector 26. Because the holes 56 will always have a finite size, a small portion of scatter 34 will reach the rear detector 26. However, as long as the size of the holes 56 is small and the thickness of the beam selector 24 is sufficiently large, this portion of scatter 34 is negligibly small in comparison with other sources of error.

Preferably, the holes 56 are as small as practical. If the holes 56 are too large, they will not prevent enough of the scatter 34 from reaching the rear detector 26. Preferably, there are as many holes as practical in the beam selector 24. The more holes 56 there are, the greater the accuracy of the measurement at the rear detector 26.

The material of the beam selector sheet 54 must ensure that all scatter 34 is absorbed and that, except for the primary x-rays 32 passing through the holes 56, none of the other radiations, including scatter 34 and secondary emissions caused either by primary x-rays 32 or by scatter 34, reach the rear detector 26.

The above-described detector assembly 14 is used to remove scatter 34 from the image as follows. A low-resolution primary x-ray image is read from selected locations 52 of the rear detector 26. The selected locations 52 are those locations on the rear detector 26 that align with the holes 56 in the beam selector sheet 54. A high-resolution composite front image is read from the front detector 22. A low-resolution composite front image is either read from or calculated from the front detector locations 58 aligned with the selected rear detector locations 52. A low-resolution scatter front image is determined by subtracting the low-resolution primary x-ray rear image from the low-resolution composite front image. A high-resolution scatter front image is calculated by interpolating the low-resolution scatter front image. The high-resolution scatter front image is subtracted from the high-resolution composite front image to produce a high-resolution primary x-ray image.

Because only the selected locations 52 on the rear detector 26 are used, an alternative structure for the rear detector 26 is to place one or more detector cells at or in the base of each hole 56 rather than using an entire 2D detector with most of it unused.

Alternatively, rather than a sheet 54 of x-ray-absorbent material with through holes 56, the beam selector 24 employs a bundle of tubes with x-ray-absorbent walls.

X-Ray Source and X Ray Measurement Device Considerations

One embodiment of the multiple-energy system is the basis-function decomposition method (the A-space method), which uses a broad-spectrum x-ray source and measures the transmitted spectrum using photon counting detectors with pulse height analysis or by using other energy-sensitive methods using energy sensitive detectors. Broad-spectrum x-ray source as in conventional x-ray source familiar to those in the art.

In another embodiment, monochromatic x-rays or x-rays of discrete energy levels are used. Such a source is generally derived by converting a broadband source using an energy filter, for example, a diffraction grating, such as a crystal, combined with a collimator. In some instances, a broadband x-ray source may be converted to a narrow band source by using a second target.

Laser-Compton and synchrotron-based quasi-monochromatic and monochromatic sources may also be used.

Newer x ray source technologies, including liquid metal target-based, cold cathode-based, and carbon nanotube-based x-ray, light such as LED, laser and ultrafast generated x ray source may all be used in the present invention.

X Ray Measurement Devices Including Photon Counting detectors, PMT and other photocounting diode and diode arrays and energy sensitive detector or energy sensitive spectrometer, in some cases, the detector measures in the x-ray spectrum. In other cases, the detector or x-ray spectrometer may measure in the visible spectrum, where an x-ray scintillator upstream of the detecting element is used to convert x-ray light to visible light. Examples of the latter may be used in x-ray full field imaging or in x-ray microscopy utilizing optical methods with light detectors.

Method of Multiple-Energy Decomposition

As to the method of the present invention, the basic methods for removing scatter and for dual-energy decomposition described in the Chao disclosures are used, and are not an aspect of the present invention. However, the method of the present invention includes improvements of these methods.

To separate a three or more material composition using the basic energy decomposition method, new procedures are required. The present invention provides a systematic method to achieve decomposition of an image of multiple components overlapping with each other into multiple-component images according to physical substance.

A component here is defined as a region which perturbs x rays differently with varied spectral levels compared to a different component or background in the region of interest. An individual image of such a component may be visualized by using dual or multiple x ray energy imaging methods.

One component or multiple component images may be generated by a user or digital program setting one or more criteria commonly used in Artificial Intelligence, neural network, such as central neural network or dynamic neural network for looking up in the reference library, so that a subset database is searched for decomposition purposes. Such process enables adoptions of deep machine learning, artificial intelligence known to those familiar with the art.

It is an aspect of the present invention to extend dual-energy decomposition method described in Chao disclosure to a multiple-energy (n>2, where n is the number of energy level) imaging system.

It is also an aspect of the present invention to extend the material calibration methods for derivation of material information in the dual-energy decomposition method described in the Chao disclosures to a multiple-energy (n>2, where n is the number of energy levels) imaging system.

It is also an aspect of the present invention to have alternative methods than the calibration method to derive material information by an existing database based on stored radiology measurement correlating with actual material or synthesized or simulated material representation from quantitative measurements derived from tomography data, such as CT, MRI, PET, SPECT.

It is also an aspect of the present invention to include previous dual-energy-based methods described in the prior art, including those for material differentiation, such as in the Chao disclosures in U.S. Pat. No. 6,173,034, using first-order approximation for multiple-energy decomposition and in some embodiments, include a second-order approximation to image a unique component, such as microcalcification, implant, a contrast-labeled component, or surgical or biopsy tools from the background tissues, as an additional new method in multiple-energy decomposition.

Calibration and Database Establishment for Material Composition Determination

In a preferred embodiment, the method of the present invention two parts: a first-order approximation and a second-order approximation.

Prior to imaging of the subject of interest, for multiple-energy material decomposition, there is a calibration and database establishment method, which involves two processes:

Process 1 is a calibration for scatter removal at various energy levels and process 2 is a database establishment for material determination using a first-order approximation, including thickness and composition. Processes 1 and 2 may be achieved through the same method, in some cases, such as the dual-detector scatter removal method described in the Chao disclosures. However, in other cases, the processes may be separate, for instance, for hardware configurations where scatter removal methods do not involve more than one detector layer. In the latter case, in some instances, calibration for scatter removal prior to the imaging of the sample may not be needed. However for x-ray measurements at each energy, scatter removal methods may be implemented in a post x-ray measurements step for the subject of interest.

In one preferred embodiment utilizing multiple-energy decomposition methods in the present invention, the first-order approximation is sufficient. The second-order approximation may be used when there is a region of a substance which fits a certain criteria, such as a component comprising contrast-labeled diseased tissue regions or calcifications, which are significantly different from its background tissues comprised of three or more physical substance. In this case, instead of using additional x-ray energy imaging methods, a second-order approximation, including calibration and post imaging processing as disclosed in the Chao disclosures, is used to derive the additional component image.

In one embodiment, the first-order approximation extends and improves scatter removal methods and material decomposition methods of a dual-energy system as described in the Chao disclosures to those for an n>2 multiple-energy system. The first-order approximation uses a basic method for the separation of primary x-rays and scatter and a basic method for multiple energy for example, En energy imaging, including dual-energy imaging, En=2, 3, 4, . . . energy imaging, to separate a mixed-component (for example, bone, microcalcification, and soft tissues such as blood vessel, fat, lean tissues) x-ray image into multiple images: an image of scatter at each energy level of multiple components, for example, in triple-energy imaging, a high-energy scatter image, a medium-energy scatter image, and a low-energy scatter image; a primary x-ray image for each component, for example, the bone tissue image, various composite or individual soft tissue images, and a microcalcification (or calcification) image if microcalcification, present or an image of an foreign object, such as an implant.

Establishment of Material Measurement Database: Various Energy Levels Prior to the Imaging of the Sample.

In one embodiment, prior to taking multiple-energy x-ray measurements of the region of interest in a subject of interest and prior to carrying out the said first-order or second-order approximation, a database is established based on a database construction method.

A new material database construction method extends the calibration method described in previous calibration systems developed for a dual-energy system to an n>2 energy system. The new database construction method allows the n-energy decomposition to provide true component images. As a result, the multiple component images are a reasonably good representation of the subject.

The database includes measurements at different x-ray spectra, designated n>2 energy levels of one or more actual materials, or materials comprised of physical substances, representing the components, composite components, or multiple overlapping components, similar to materials in the sample to be measured. The database includes x-ray measurements of static composition or structure, such as bone, muscle, or characteristic composition or structure at each signature stage of a dynamic cycle, such as cardiovascular-related muscle movement, such as cardiac movements or dynamic process of one or more regions of one or more component or component composites in the region of interest, such as accumulation of cation ions due to cell death, or diseased tissues, similarly, various states of one or more material in the component, for example, tissue region of energy ablated regions or temporal markers of the same component including characteristic static and dynamic physical properties in multiple dimensions, such as presence and absence of material or density variation during a physiological changes, dynamic physiological properties in multiple dimensions. Measured x-ray data includes those which are descriptive of physical and chemical properties, including that of varied thickness, compositions, densities, multiple-dimension structures, or other properties perturbed differently by various x-ray spectral measurements.

In some instances, certain segments of the database may be provided by stored data or real-time measurements. For example, components such as an implant, surgical tool, chemical compound, or any object that has well-defined physical and chemical properties or x-ray measurement properties and dimensions, may be provided as part of database. For example, x-ray measurements at various thicknesses of a certain materials may be provided. In some instances, thickness measurements and geometry and dimension measurements of one or more components may be derived in real time due to x-ray measurements in multiple dimensions, with multiple energies, or measurements from a different spatial position sensing device known to those familiar with the prior art.

In addition to the establishment of a database by a user carrying out a calibration step involving pre-imaging measurement, such a database or part of the database may be derived from existing databases based on stored radiography measurements correlating with actual materials, including air cavity measurements contained in the region of interest, if relevant, or synthesized or simulated material or air cavity representations from quantitative measurements derived from multiple-dimensional radiography data or tomography data, such as CT, Sinogram, Mill, PET, SPECT, optical Imaging, acoustic, photoacoustic, spectroscopy, and other energy, electron- and chemistry-triggered measurements.

In some embodiments, dual-energy-based or smaller than n number of energy level database maybe sufficient for n>2 energy imaging-based material decomposition methods. In some instances, relevant physical properties and dimension information about the component(s) or the region of interest may be known or may be able to be derived and simulated, as a result, such database may not be necessary Quantitative Relationships Between Sensing Elements of Each Detector Used in the System, Especially Those Correlating Measurements of the Same Illumination Projected Path.

In one embodiment, when dual or more detector layers or sensing elements are used, for example, the aforementioned Chao disclosures, or any dual- or multiple-sensing elements along the same x-ray projected path, the database may include measurements from a calibration method that establishes a quantitative relationship database between the front detector and rear detector or detectors. In some cases, only at selected locations, for example (i,j) and (i',j'). When the front detector is reasonably similar to or basically the same as the rear detector, such calibration methods to correlate measurements on the front detector, for example, the primary x-ray measurement, to that measured on the rear detector, may be simplified by using existing algorithms to characterize the relationship of the front detector and the back detector. When there is relevant data available for the type of detector used, for the purpose of scatter removal, such relationship information may be simulated or derived without the calibration step.

Step 1. First-Order Approximation

The method of obtaining the first-order approximation includes the following eight steps:

(a) Perform a calibration for materials M. In chest imaging, for example, the first component M1 is a stent or implant, M2 is bone, m3 is soft tissue, M4 is blood vessels, and M5 is calcification.

$$M_1=M_1(D1\ldots Dn)$$

$$M_2=M_2(D1\ldots Dn)$$

$$Mn=Mn(D1\ldots Dn)$$

For simplification purposes, a dual-energy imaging of the breast is used here for illustration, As described below, to obtain a pair of numerical relationships for the front detector at the high energy and the low energy for the microcalcification or calcification c and the soft tissue s to obtain the functions $c=c(D_H,D_L)$ and $s=s(D_H,D_L)$, additional energy levels may be applied for other tissues. For example, the equation would be $c=c(D_1,D_2,D_3)$, $s=s(D_1,D_2,D_3)$, $b=b(D_1,D_2,D_3)$, ... $l=l(D_1,D_2,D_3)$, where b represents the equation for bone and l represents the equation for contrast-labeled tissue. $D_H,D_L$ are representatives of $D_1$ and $D_2$, respectively. However for simplification purposes, only two components and two energy methods are illustrated. Such dual methods may be extended to multiple energy systems. As the below description are linearized basis functions, therefore if number of unknowns corresponds to the number of equations, the basic principles are similar.

(b) Perform a calibration to obtain a pair of numerical relationships for the front detector at two energies, for the first component f and the second component g, in the example, fat tissue and the lean tissue, respectively, to obtain the functions $f=f(D_H,D_L)$ and $g=g(D_H,D_L)$.

Note that part of or all calibration needed may be replaced by database-derived from previous measurements and simulated data of multiple-energy radiography, CT tomography, Sinogram in CT and other modalities such as Mill, Single Photon Emission CT, PET, spectroscopy, and optical measurements as described above. In the Chao's disclosures, the calibration for scatter removal which also involves front and rear detector scalar relationship derivation, calibration for material decomposition which provides for thickness and composition based information, are performed together. In the present invention, the two calibrations may be separated, and database for material decomposition look up may be performed as a separate method from that for scatter removal, for instance, in the case of a single-detector, single-energy-based scatter removal method. For illustration purposes, the dual-detector methods and hardware are described. But other non-dual-detector-based scatter removal methods maybe employed as well.

(c) Illuminate the subject with x-rays of energy level H and of energy level L.

(d) Acquire high-resolution images $D_{fHh}(x,y)$ and $D_{fLh}(x,y)$ from the front detection locations (x,y), where the images are composed of both primary and scatter x-rays.

(e) Calculate a pair of high-resolution scatter x-ray images $D_{fSHh}(x,y)$ and $D_{fSLh}(x,y)$.

(f) Calculate a pair of high-resolution primary x-ray images $D_{fSHh}(x,y)=D_{fHh}(x,y)-D_{fSHh}(x,y)$ and $D_{fPLh}(x,y)=D_{fLh}(x,y)-D_{fSLh}(x,y)$.

(g) Perform a dual-energy decomposition for the image pair $D_{fPHh}(x,y)$ and $D_{fPLh}(x,y)$ using the functions $c=c(D_H, D_L)$ and $s=s(D_H,D_L)$ to obtain two first-order approximation material composition images $c_1(x,y)$ and $s_1(x,y)$.

(h) Perform a dual-energy decomposition for the image pair $D_{fPHh}(x,y)$ and $D_{fPLh}(x,y)$ using the functions $f=f(D_H,D_L)$ and $g=g(D_H,D_L)$ to obtain two first-order approximation material composition images $f_1(x,y)$ and $g_1(x,y)$.

The present invention includes the utilization of above-described database or calibration methods.

In one embodiment, the present invention includes a second order approximation step.

A quantitative relationship algorithm may be established prior to the imaging of the subject. To establish such a database, a calibration method for the second order approximation step is used. The calibration method of the present invention includes the steps of (1) determining a dual-energy equation system for two known materials u and v as DH=DDH[u,v], DL=DDL[u,v], (2) conducting functional decomposition for energy-dependent attenuation coefficient functions $\square u(E)=up\square \square p(E)+uq\square \square q(E)$ and $\square v(E)=vp\square \square p(E)+vq\square \square q(E)$ using standard least-square data fitting methods to obtain constants up, uq, vp, and vq, (3) calculating $p=u \square (up+vp)$ and $q=v \square (uq+vq)$ for each coordinate pair (u,v) to obtain the dual-energy equation system DH=DDH[p,q], DL=DDL[p,q], and (4) solving the equation system DH=DDH[p,q], DL=DDL[p,q] for the materials p and q as a function of variable pair (DH,DL) through numerical inversion to obtain the equation system p=p[DH,DL] and q=q[DH,DL].

Although the first-order approximation provides reasonably good component images, improvements are still possible.

For example, in lung imaging, because the chest is composed of three or more tissue components, a simple dual-energy decomposition has limitations. Some of the component images obtained in the first-order approximation still contain a small portion of mixed signals and are not pure single-component images.

In the second-order approximation, in the case of chest imaging, microcalcification in the lung, or a foreign defined component, soft tissue including fat and lean tissues, bone image are generated, taking the multiple-material compositions of the chest into account.

Separation of Distinct and Rare Component (DRC)

In the present specification, a DRC is unlike the rest of the region of interest. Examples include microcalcification or calcification regions, implants, and contrast-labeled components. Distinct components have not only unique physical compositions and dimensions, but are also different in terms of some critical properties compared to that of the rest of region of interest. Examples of critical properties include, in the case of contrast-labeled components or microcalcification, a lack of slowing varying properties of tissues. The distinct component can be relatively rare and much smaller in dimension than other components in the region of interest. The DRC component may be embedded in a multiple-component region where a tissue or multiple tissues have similar x-ray-measured properties, but different from that of the DRC component, for example, similar atomic Z, as in soft tissue. One or several such differentiable properties may differentiate the DRC component from the rest of the components in the region. The DRC component may be corrected using second-order approximations.

The method of obtaining the second-order approximations corrects for DRC component effects and includes the steps of (a) identifying all DRC component, or in this example, microcalcification, points $c_1(x_k,y_k)$ and all non-DRC component identifier points $c_1(x_i,y_i)$ in the image $c_1(x,y)$, (b) constructing a background image B(x,y) where points $B(x_i,y_i)=c_1(x_i,y_i)$ and where points $B(x_k,y_k)$ are interpolated from points $c_1(x_j,y_j)$ around points $c_1(x_k,y_k)$, (c) subtracting the background image B(x,y) from the image $c_1(x,y)$ to obtain a second-order approximation unique identifier image $c_2(x,y)$, (d) identifying all zero points $c_2(x_o,y_o)$ and non-zero points $c_2(x_m,y_m)$ in the image $c_2(x,y)$, (e) constructing a second-order approximation image $f_2(x,y)$ of a first unique tissue, such as fat or lean tissue or soft tissue, where points $f_2(x_o,y_o)=f_1(x_o,y_o)$ and where points $f_2(x_m,y_m)$ are interpolated from points $f_1(x_n,y_n)$ around points $f_1(x_m,y_m)$, and (f) constructing a second-order approximation image $g_2(x,y)$ of a second unique tissue, such as bone tissue, where points $g_2(x_o,y_o)=g_1(x_o,y_o)$ and where points $g_2(x_m,y_m)$ are interpolated from points $g_1(x_n,y_n)$ around points $g_1(x_m,y_m)$.

Extension of Dual-Energy Decomposition First-Order Approximation

Figure 4:
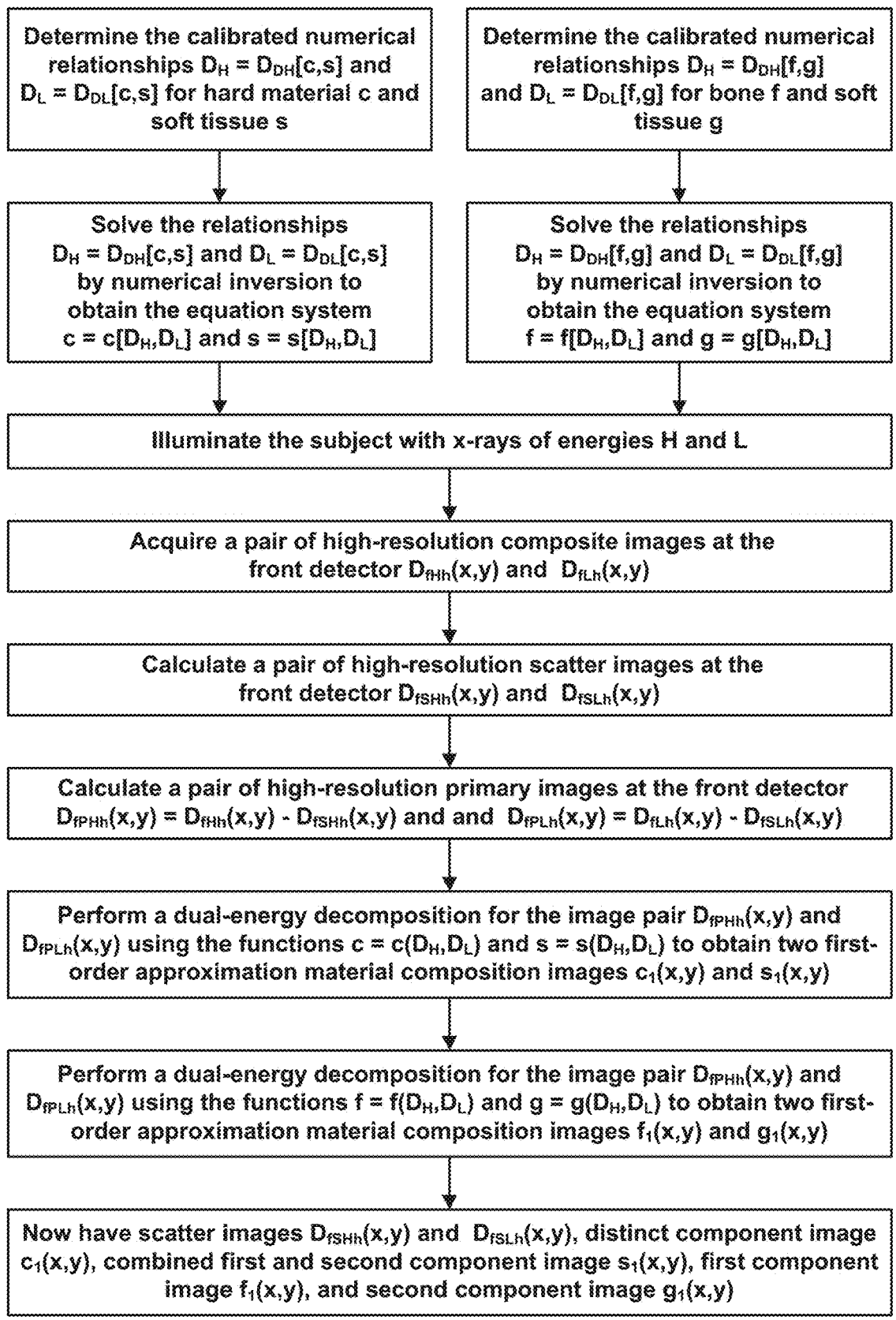
FIG. 4 is a flow diagram of the method for performing a dual-energy decomposition of an image into first-order-approximation component images.
Figure 5:
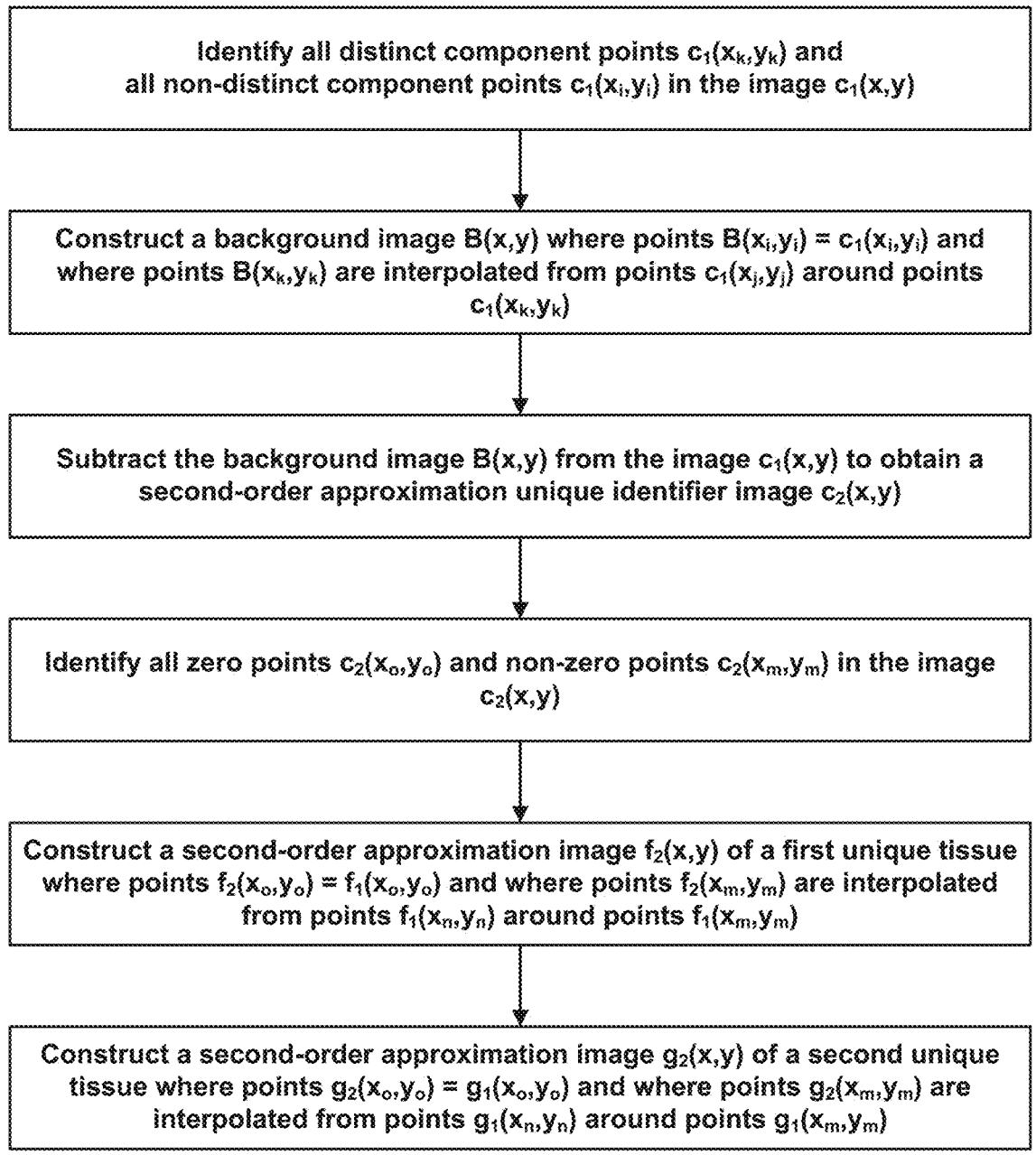
FIG. 5 is a flow diagram of the method for performing a dual-energy decomposition of an image into second-order-approximation component images.

The steps of the first-order approximation are shown in the flow diagram of FIG. 4. The first step is to perform two calibrations for different material pairs under the same system conditions.

The first calibration is to obtain a pair of numerical relationships for the front detector at the high-energy level H and the low-energy level L for two materials c and s, where c denotes the material having an x-ray attenuation coefficient as a function of x-ray energy $\square_c(E)$ that is the same as that of microcalcification deposits, and s denotes the material having an x-ray attenuation coefficient as a function of x-ray energy $\square_s(E)$ that is the same as that of an average tissue substance.

The following is a description of how to perform dual-energy calibration for true tissue components, which are now extended for utilization and in some cases, improved in multiple-energy imaging in the present invention.

Dual-energy calibration methods are described in detail in the Chao disclosures. When there are multiple energy systems, this can be extended to a multiple energy system calibration. In the present invention, the calibration may be conducted regarding the actual material composition.

For conducting calibration measurements, according to the methods described in the Chao disclosures, a number of material plates of the two composition materials should be used in the calibration measurements. Currently, such standard tissue samples have not been available. The present invention provides an improved multiple-energy calibration method that can use another pair of materials for calibration measurements to obtain the accurate calibration data for the desired different material pair.

The scientific foundation of the improved calibration method is described below.

Assume that it is desired to obtain numerical equations for the calibration data material pair of (p,q), but the direct material (p,q) data is not available due to certain practical limitations. On the other hand, another material pair (u,v) is available for use in the calibration measurements. Also, all of the x-ray attenuation coefficients as x-ray energy functions $\mu_u(E)$, $\mu_v(E)$, $\mu_p(E)$ and $\mu_q(E)$ are known. In breast imaging, the (u,v) material pair can be, for example, a pair of commercially available materials, such a polyethylene (CH$_2$) sheet and water (H$_2$O). More materials may be used for additional components, for example, commercially-available materials, such as aluminum and acrylic.

Note that the material pair may be two or more in the present invention. And the number of known materials used in a material set for the second-order approximation, even in a multiple-energy system, may be between 2 and n, and the corresponding energy levels used in the second-order approximation are also between 2 and n. For example, microcalcification in the lung may be separated from chest bone, lung tissue, other soft tissues. In this case, multiple-energy imaging is used to separate microcalcification from the lung tissue, there may be only three known material sets that need to be calibrated, u, v, w. The first set of relationships is microcalcification c, lung plus soft tissue composite l, and bone b. The second set of relationships is bone b, lung l, and other soft tissue s.

The number of known materials may vary and the number of materials may selected as separate composites for calibration and second-order approximation, but the basic principle is similar.

In another embodiment, when the 2D projected image has measurements of the same component type or similar materials from two locations in the projected path, for example, measurements of a region of bone that overlap with a microcalcification region on the projected image in chest imaging, the edge between the overlap and no overlap may have a measurable difference in bone density or thickness measurements. Microcalcification quantification may be achieved by statistically analyzing bone density measurements in the regions surrounding the estimated region where there is an overlap. Since non-overlapped regions and overlapped regions are slowly varying, therefore similar in density and dimension, the bone density and dimension measurements of the overlapped region may be interpolated based on adjacent regions. The measurement for the microcalcification region then can be derived.

Alternatively, if multiple-dimension images are taken and synthesized, the region with bone images and the region with the microcalcification images may be resolved from one another. Accurate density measurements and thickness measurements may be derived.

Alternatively, for example, in the imaging of microcalcification in chest imaging, the amount of microcalcification may be estimated from a dual-energy method by taking an x-ray image of the selected region from an illumination path which does not go through the bone regions of the body. In this case, only dual-energy first-order and second-order approximation methods required as only lung tissue and other soft tissues along the project x-ray path may be considered.

In another example, in breast imaging, both tumor label and microcalcifications may be separated by using two energies. Using three-energy methods, breast tissues may be separated into fat, lean, and tumor-labeled regions. When calibrated with three known materials, u, v, w and at three different energy levels, solving for calcification, tumor, and fat and lean tissue composite, and solving for calcification, tumor and lean tissue composite, and fat tissue would provide additional information for the diagnosis.

Going back to the example of the dual-energy system, the dual-energy equation system is written as $$D_{fPHh}(x,y) = \int [\mu_{OH}(E) \cdot \exp(-(\mu_u(E) \cdot u(x,y) + \mu_v(E) \cdot v(x,y))] \cdot S_f(E) dE \quad (1a)$$

$$D_{fPLh}(x,y) = \int [\mu_{OL}(E) \cdot \exp(-(\mu_u(E) \cdot u(x,y) + \mu_v(E) \cdot v(x,y))] \cdot S_f(E) dE \quad (1b)$$

where $\mu_{OH}(E)$ and $\mu_{OL}(E)$ are the energy spectra of the x-ray source 14 at the higher energy level H and the lower energy level L, respectively. The projection mass densities u(x,y) and v(x,y) are in units of gram/centimeter$^2$ (g/cm$^2$). The mass attenuation coefficients $\mu_u(E)$ and $\mu_v(E)$ are expressed in units of centimeter/gram (cm$^2$/g). All of these values are known. Sf(E) is the x-ray spectral sensitivity of the front detector.

Conduct functional decomposition for the energy-dependent attenuation coefficient functions $\mu_u(E)$ and $\mu_v(E)$ $$\mu_u(E) = u_p \cdot \mu_p(E) + u_q \cdot \mu_q(E) \quad (2a)$$

$$\mu_v(E) = v_p \cdot \mu_p(E) + v_q \cdot \mu_q(E) \quad (2b)$$

where the constants $u_p$, $u_q$, $v_p$, and $v_q$ can be obtained through standard least-square data fitting methods. It should be noted that such functional decomposition cannot be generally true from a mathematics point of view. However, it has been established through extensive analysis of experimental data that, for substances composed of chemical elements with low to medium atomic number Z, such as carbon, hydrogen, oxygen, nitrogen, up to calcium, as in the human body, and as long as the x-ray energy is within the medical diagnostic energy range, such as between 20 keV and 150 keV, a third x-ray mass attenuation function can always be written as a sum of two other x-ray mass attenuation functions with good approximation. The energy-dependent attenuation function in the exponent of the exp( ) of equations (1a) and (1b) is denoted UF(E):

$$-UF(E) = \mu_u(E) \cdot u(x,y) + \mu_v(E) \cdot v(x,y) \quad (3)$$
$$= [u(x,y) \cdot u_p + v(x,y) \cdot v_p] \cdot \mu_p(E) +$$
$$[u(x,y) \cdot u_q + v(x,y) \cdot v_q] \cdot \mu_q(E) +$$

where $$u(x,y) \cdot u_p + v(x,y) \cdot v_p \equiv p(x,y) \quad (4a)$$

and $$u(x,y) \cdot u_q + v(x,y) \cdot v_q \equiv q(x,y) \quad (4a)$$

where the symbol "≡" represents definition, then $$-UF(E) = \mu_p(x,y) + \mu_q(E) \cdot q(x,y) \quad (5)$$

Therefore, the procedure for the improved calibration includes the following steps:

(1) Conduct calibration measurements by using the (u,v) material pair as described in the Chao disclosures. As a result, this numerical equation system is obtained:

$$D_H = D_{DH}[u,v] \quad (6a)$$

$$D_L = D_{DL}[u,v] \quad (6b)$$

(2) Conduct functional decomposition for the energy dependent attenuation coefficient functions $\mu_u(E)$ and $\mu_v(E)$ $$\mu_u(E) = u_p \cdot \mu_p(E) + u_q \cdot \mu_q(E) \quad (7a)$$

$$\mu_v(E) = v_p \cdot \mu_p(E) + v_q \cdot \mu_q(E) \quad (7b)$$

by using standard least-square data fitting methods, and obtain the constants $u_p$, $u_q$, $v_p$, and $v_q$.

(3) For each data pair (u,v) in equations (6a),(6b), calculate $$u\Box u_p + v\Box v_p = p \quad (8a)$$

$$u\Box u_q + v\Box v_q = q \quad (8b)$$

and obtain a new dual-energy numerical equation system $$D_H = D_{DH}[p,q] \quad (9a)$$

$$D_L = D_{DL}[p,q] \quad (9b)$$

(4) Solve the equation system $D_H=D_{DH}[p,q]$ and $D_L=D_{DL}[p,q]$ for the variable pair [p,q] as a function of the variable pair $[D_H, D_L]$ through numeric inversion and obtain $$p = p[D_H, D_L] \quad (10a)$$

$$q = q[D_H, D_L] \quad (10b)$$

For performing two types of dual-energy decomposition, two corresponding types of calibration are conducted. The first type of calibration is for the material pair (c,$) for the DRC component, in this case, microcalcification, and the other types of tissues in the region of interest, in this case, soft tissue. By using the above-described calibration procedures, a pair of quantitative explicit numerical functions $$D_H = D_{DH}[c,s] \quad (11a)$$

$$D_L = D_{DL}[c,s] \quad (11b)$$

are established, where the notations $D_H[\ ]$ and $D_L[\ ]$ represent functional relationships with c and s as variables. The equation system is solved by, for example, numerical inversion to obtain a numerical equation system $$c = c[D_H, D_L] \quad (12a)$$

$$s = s[D_H, D_L] \quad (12b)$$

This numerical equation system is applicable to all normalized pixels. From the measured signal pair $(D_H, D_L)$ for any pixel, the material composition data pair c and s for that pixel can be readily found.

The second type of calibration is to obtain a pair of numerical relationships for the detector at the high-energy level H and the low-energy level L for two materials f and g, where f denotes the material having an x-ray attenuation coefficient $u_f(E)$ the same as that of a first tissue or a first component in the region of the interest, and g denotes the material having an x-ray attenuation coefficient $u_g(E)$ the same as that of a second tissue or a second component. Thus, the quantitative explicit functions $$D_H = D_{DH}[f,g] \quad (13a)$$

$$D_L = D_{DL}[f,g] \quad (13b)$$

are established. The equation systems is solved by, for example, numerical inversion to obtain a numerical equation system $$f = f[D_H, D_L] \quad (14a)$$

$$g = g[D_H, D_L] \quad (14b)$$

This numerical equation system is applicable to all normalized pixels. From the measured signal pair $(D_H, D_L)$, the material composition data pair (f,g) can be readily found.

To avoid misunderstanding, two points need to be mentioned. First, for better accuracy, the calibration materials should be chosen to have a composition as close as possible to the actual tissue compositions in terms of x-ray interaction. This should be clear based on general error theory for experimental measurements. For example, when $\Box_u(E)$ is close to $\Box_p(E)$ and $\Box_v(E)$ is close to $\Box_q(E)$, the error due to transformation of (7a) and (7b) is smaller.

The second point is that there exists a number of trivial alternatives to the order of the calculation steps. For example, after step (1), conducting calibration measurements by using the (u,v) material pair and establishing the numerical relationships (6a) and (6b), instead of performing a material pair transformation (8a) and (8b) to obtain the numerical relationships (9a) and (9b), one can directly conduct the inversion for the (6a) and (6b) to obtain $$u = u[D_H, D_L] \quad (15a)$$

$$v = v[D_H, D_L] \quad (15b)$$

Then, applying the relationships (15a) and (15b) to the image data, $D_{fPHh}(x,y)$ and $D_{fPLh}(x,y)$, two material images u(x,y) and v(x,y) can be obtained. After that, by using the equations (8a) and (8b)

$$p(x,y) = u(x,y)\Box u_p + v(x,y)\Box v_p \quad (16a)$$

$$q(x,y) = u(x,y)\Box u_q + v(x,y)\Box v_q \quad (16b)$$

the entire images u(x,y) and v(x,y) are transformed, point by point, into two images p(x,y) and q(x,y). This is only a trivial variation of the order for mathematical calculations without any essential change of the method. Therefore, it is contemplated that the procedures as described in equations (1a),(1b) through (12a),(12b) include these and other similar trivial alternatives.

The second step of the method of the present invention is to acquire a pair of high-spatial-resolution composite images of the front detector $D_{fHh}(x,y)$ and $D_{fLh}(x,y)$, where the subscript f denotes an image of the front detector, subscript H denotes a high-energy-level image, subscript L denotes a low-energy-level image, subscript h denotes a high-resolution image, and (x,y) denotes the two-dimensional Cartesian coordinates of a detector cell of the front detector. Each of the images in image data pair $D_{fHh}(x,y)$ and $D_{fLh}(x,y)$ contains a scatter component and a primary x-ray component. The primary x-ray component contains a first component, a second component, and a DRC component.

The third step is to separate each image of the image pair $D_{fHh}(x,y)$ and $D_{fLh}(x,y)$ into the scatter component and primary x-ray component. This is done through a number of data acquisition and calculation steps, as described in the Chao disclosures, to calculate a pair of high-spatial-resolution, scatter-only images at the front detector $D_{fSHh}(x,y)$ and $D_{fSLh}(x,y)$, where the subscript S denotes a scatter-only image. This step is the same as the corresponding step in the Chao disclosures.

The fourth step is to calculate the high-spatial-resolution primary x-ray image pair $D_{fPHh}(x,y)$ and $D_{fPLh}(x,y)$ from the equations $$D_{fPHh}(x,y) = D_{fHh}(x,y) - D_{fSHh}(x,y) \quad (17a)$$

$$D_{fPLh}(x,y) = D_{fLh}(x,y) - D_{fSLh}(x,y) \quad (17a)$$

where the subscript P denotes primary x-ray-only image. This step is also the same as described in the Chao disclosures.

The fifth step is to perform a dual-energy decomposition for the image pair $D_{fPHh}(x,y)$ and $D_{fPLh}(x,y)$ by using the calibrated numerical equation system (12a), (12b). As a result, two material composition images $c_1(x,y)$ and $s_1(x,y)$ are obtained. In this image pair, $c_1(x,y)$ is basically a DRC component image and $s_1(x,y)$ is basically an image of the composite material of the first component and the second component.

The sixth and final step is to perform a dual-energy decomposition for the image pair $D_{fPHh}(x,y)$ and $D_{fPLh}(x,y)$ by using the calibrated numerical equation system (14a), (14b). As a result, two material composition images $f_1(x,y)$ and $g_1(x,y)$ are obtained. In this image pair, $f_1(x,y)$ is basically a first component image and $g_1(x,y)$ is basically a second component image. However, both $f_1(x,y)$ and $g_1(x,y)$ may contain the DRC component information, which has not been explicitly specified and appropriately quantified.

At this point, usable results have been obtained by the decomposition of a single image into five component images: the scatter image $D_{fS}(x,y)$, the DRC component image $c_1(x,y)$, the image of combined material with both first and second component $s_1(x,y)$, the first component image $f_1(x,y)$, and the second component image $g_1(x,y)$. However, the power of dual-energy decomposition has not yet been fully exploited. The above results may be considered as a good first approximation for general imaging data. The reason that these component images can only be considered as first approximation is because that, in performing the above procedures of dual-energy decomposition, the region of interest is assumed to be composed of only two materials. The region of interest is actually comprised of three materials.

Dual-Energy Decomposition Second-Order Approximation Extended to Multiple-Energy Systems: DRC Imaging The next part of the present specification describes a method for second-order approximation to take into account three or more material components, for example, in chest or heart imaging or imaging of a subject comprised of three or more components. First, the scientific principles are explained, and then the steps of the method are described.

In this embodiment, where dual-energy methods may be used as described in this present specification, a three-material image decomposition method, which is based on images taken with x-rays of two different energies may have the advantage of lower radiation levels and faster acquisition time.

In situations where there are more components t>n+1 where n is the available energy levels, the current method may also be used to separate the additional component(s) from the rest.

The following explains how to use the n-energy method to approximately separate n+1 or more components in a region of interest in medical imaging or industrial imaging. This is possible because there are special conditions of the medical imaging that can be utilized to achieve a good approximation. The first special condition is that the x-ray attenuation of at least 2 components out of n components are very close when compared to that of the DRC component, the n+1th component. The second condition is that the DRC component, such as microcalcification deposits, or calcification regions, implant regions, or contrast agent labeled diseased regions, generally exist in much smaller, in some instances, isolated regions, and lacking the slowly varying properties of the tissues or components in the rest of the region of interest. For example, microcalcification, will be within only few single image pixels.

For example, when n=2, the dual-energy imaging equation of the region of interest can be represented by the equation pair $$D_{fPHh}(x,y) = \square[\square_{0H}(E)\square \tag{18a}$$
$$\exp(-(\square_c(E)\square c(x,y)+\square_f(E)\square f(x,y)+\square_g(E)\square g(x,y))]$$
$$\square S_f(E)dE$$

$$D_{fPHh}(x,y) = \square[\square_{0L}(E)\square \tag{18a}$$
$$\exp(-(\square_c(E)\square c(x,y)+\square_f(E)\square f(x,y)+\square_g(E)\square g(x,y))]$$
$$\square S_f(E)dE$$

The projection mass densities $c(x,y)$, $f(x,y)$, and $g(x,y)$ of the subject are in units of gram/centimeter$^2$ (g/cm$^2$). The mass attenuation coefficients $\square_c(E)$, $\square_f(E)$, and $\square_g(E)$ are known and expressed in units of centimeter/gram (cm$^2$/g). The energy-dependent exponent of the exponential function exp( ) in equation system (18a),(18b) is denoted as AF(E), and is $$-AF(E)=\square_c(E)\square_c(x,y)+\square_f(E)\square f(x,y)+\square_g(E)\square g(x,y) \tag{19}$$

There are three independent mass attenuation functions, $\square_c(E)$, $\square_f(E)$, and $\square_g(E)$, connected by three unknown parameters for material density values $c(x,y)$, $f(x,y)$, and $g(x,y)$. Dual-energy measurements only provide two measured signals $D_{fPHh}(x,y)$ and $D_{fPLh}(x,y)$, from which only two unknown parameters can be determined.

The basic method used for quantitative evaluation of each tissue component is a method of functional decomposition. One energy-dependent mass attenuation function must be expressed as a sum of the other two functions. For example, to perform a basic dual-energy decomposition for a first and second component, the DRC component function, for example, calcium function, $\square_c(E)$ is decomposed as $$\square_c(E)=R_{cf}\square\square_f(E)+R_{cg}\square\square_g(E) \tag{20}$$

where $R_{cf}$ and $R_{cg}$ are constants. Note that for the human body system, where the x-ray energy is within medical diagnostic energy range, the third x-ray mass attenuation function can always be written as a sum of the other two x-ray mass attenuation functions with good approximation. The exact values of $R_{cf}$ and $R_{cg}$ can be calculated by using standard least-square data fitting methods. For example, within an x-ray energy range of 16 keV and 100 keV, by applying least-square data fitting methods to equation (20), it can be found that $R_{cf}\approx-34$ and $R_{cg}\approx33$. Accurate values of the $R_{cf}$ and $R_{cg}$ are dependent on the x-ray energy range used in the hardware system.

Some general observations can be made regarding the parameter pair $R_{cf}$ and $R_{cg}$. First, $R_{cf}$ is always negative and $R_{cg}$ is always positive. Second, the absolute values of $R_{cf}$ and $R_{cg}$ are always rather large and are always close to each other. For example, for the diagnostic energy range, the absolute value of $R_{cf}$ and $R_{cg}$ can be assumed to be between 10 to 50. The underlying physical reason for these two characteristic features comes from the fact that calcium has a much larger attenuation coefficient at lower energies than various soft tissues, and at the low energies, the soft tissues of various types generally have similar attenuation coefficients and have a slightly larger attenuation coefficient than that of fat. These characteristic features produce very uncommon results in the decomposed component x-ray images: when the image is decomposed into separate soft tissue component images, each DRC component region, such as implant or microcalcification, produces a positive high-intensity attenuation change in the first component image, such as lean tissue image, and each DRC component region produces a negative high-intensity attenuation change in the second component tissue image at that point. These positive and negative points have an exact quantitative relationship. For example, one microgram of microcalcification produces a positive attenuation change corresponding to approximately 30 micrograms of lean tissue intensity change, and a negative attenuation change corresponding to approximately 30 micrograms of the first soft tissue intensity change. These characteristic features are utilized in the present invention for quantitatively separating the superimposed microcalcification image from the first soft tissue component image and from the second soft tissue component image.

AF(E) can be again be written in a form that contains only two basis functions $$-AF(E)=\mu_f(E)\cdot[f(x,y)\cdot R_{cf}\cdot c(x,y)]+\mu_g(E)\cdot[g(x,y)\cdot R_{cg}\cdot c(x,y)] \qquad (21)$$

or $$-AF(E)=\mu_f(E)\cdot fc(x,y)+\mu_g(E)\cdot gc(x,y) \qquad (22)$$

where $$fc(x,y)=f(x,y)\cdot R_{cf}\cdot c(x,y) \qquad (23a)$$

$$gc(x,y)=g(x,y)\cdot R_{cg}\cdot c(x,y) \qquad (23b)$$

Because AF(E) contains only two independent functions $\mu_f(E)$ and $\mu_g(E)$, by using dual-energy decomposition procedures as described in the Chao disclosures, two unique energy-independent parameters can be obtained through solving equation system (18a) and (18b), the solution pair is fc(x,y) and gc(x,y). Note that the solution pair fc(x,y) and gc(x,y) are exactly the solution pair of the first approximation. That is $$f_1(x,y)=fc(x,y)=f(x,y)\cdot R_{cf}\cdot c(x,y) \qquad (24a)$$

$$g_1(x,y)=gc(x,y)=g(x,y)\cdot R_{cg}\cdot c(x,y) \qquad (24b)$$

After performing dual-energy decomposition according to the procedures of the first order approximation, the third material component is projected and superimposed onto the two basis component images as expressed in (24a) and (24b), as $R_{cf}\cdot c(x,y)$ on the fat tissue image and as $R_{cg}\cdot c(x,y)$ on the lean tissue image. Generally speaking, the portion of superimposed third-component image cannot be separated from the two-component images because only fc(x,y) and gc(x,y) can be calculated by using dual-energy decomposition.

The present invention utilizes certain characteristic specific conditions for medical imaging to approximately separate the third-material composition. For example, in lung imaging, it is known that, the microcalcification deposits exist only in small regions. For a small region, the soft tissue density can be assumed to change approximately smoothly. The following is an outline of the basic steps of separating microcalcification image spots from the soft tissue image. First, identify the microcalcification spots on the image. The microcalcification spots must be (a) a positive signal/negative signal pair, each having approximately equal absolute values of amplitude, but having opposite signs, and (b) superimposed at exactly the same corresponding locations on the first soft tissue component image and the second soft tissue component image. Second, interpolate an image intensity from nearby surrounding soft tissue pixels to replace the image intensity of these suspected microcalcification spots. Third, subtract the interpolated signal intensity from the original signal intensity, gc(x,y) and fc(x,y), at the identified spot to determine if the intensity change is consistent with that predicted by decomposition equation (20) for the microcalcification function. If the microcalcification intensity on the two soft tissue images are quantitatively consistent with that predicted by the equation (20), the spot meets the preliminary test for a microcalcification spot. For other DRC component measurements, similar methods can be used.

In addition to this preliminary test, there is a further test, to be described below.

The following is a description of the scientific foundation of how to obtain a pure DRC component image through a second decomposition.

Using microcalcification measurement as an example, in the second decomposition at the accuracy level of first-order approximation, the two basis functions are chosen to be $\mu_c(E)$ and $\mu_{sa}(E)$, where $\mu_c(E)$ is the energy-dependent attenuation function for microcalcification and $\mu_{sa}(E)$ is the attenuation function for an average soft tissue composition. Two images, $c_1(x,y)$ and $s_1(x,y)$, are obtained as a result of the second decomposition at an accuracy level of first-order approximation. In the first-order approximation, it was assumed that there were only two material compositions with the mass attenuation coefficient functions $\mu_c(E)$ and $\mu_{sa}(E)$. According to the actual soft tissue material composition, the energy-dependent exponent in the equations (18a), (18b) is denoted as BF(E):

$$-BF(E)=\mu_c(E,y)+\mu_f(E)\cdot f(x,y)+\mu_g(E)\cdot g(x,y) \qquad (25)$$

or $$-BF(E)=\mu_c(E)\cdot c(x,y)+\mu_{sa}(E)\cdot s_a(x,y)+\delta\mu_s(E)\cdot\delta s(x,y) \qquad (26)$$

where the average tissue mass attenuation coefficient function $\mu_{sa}(E)=50\%\ \mu_f(E)+50\%\ \mu_g(E)$. $\delta\mu_s(E)\cdot\delta s(x,y)$ is the local deviation at the pixel (x,y) from the averaged soft tissue attenuation $\mu sa(E)\cdot s_a(x,y)$. For example, when the tissue composition at (x,y) is exactly 50% fat tissue and 50% lean tissue, then $\delta\mu_s(E)=0$. Otherwise, for performing dual-energy decomposition according to the basis functions $\mu_c(E)$ and $\mu_{sa}(E)$, the energy-dependent function $\delta\mu_s(E)$ must be decomposed into two basis functions $\mu_c(E)$ and $\mu_{sa}(E)$ as $$\delta\mu s(E)=R_{sc}\cdot\mu c(E)+R_{ss}\cdot\mu_{sa}(E) \qquad (27)$$

where $R_{sc}$ and $R_{ss}$ are two constants, the exact values of which can be calculated by using standard least-square data fitting methods when the local tissue composition is known. Then, $$-BF(E)=\mu_c(E)\cdot[c(x,y)+R_{sc}\cdot\delta s(x,y)]+\mu_{sa}(E)\cdot[S_a(x,y)R_{ss}\cdot\delta s(x,y)] \qquad (28)$$

or $$-BF(E)=\mu_c(E)\cdot cs(x,y)+\mu_{sa}(E)\cdot ss(x,y) \qquad (29)$$

where $$cs(x,y)=c(x,y)+R_{sc}\cdot\delta s(x,y) \qquad (30a)$$

$$ss(x,y)=s_a(x,y)+R_{ss}\cdot\delta s(x,y) \qquad (30b)$$

Some general observations can be made regarding the parameter pair $R_{sc}$ and $R_{ss}$. First, $R_{sc}$ is much smaller than 1.0 and $R_{ss}$ is not much different from 1.0. The underlying physical reason stems from the fact that the energy-dependent behavior of the function $\delta\Box_s(E)$ is not much different from that of the average tissue function $\Box_{sa}(E)$ and very much different from that of $\Box_c(E)$.

Note that the dual-energy decomposition results obtained at the accuracy level of the first-order approximation $c_1(x,y)$ is exactly $cs(x,y)$ and that $s_1(x,y)$ is exactly $ss(x,y)$. That is, $$c_1(x,y)=cs(x,y)=c(x,y)+R_{sc}\Box\delta s(x,y) \quad (31a)$$

$$s_1(x,y)=ss(x,y)=s_a(x,y)+R_{ss}\Box\delta s(x,y) \quad (31b)$$

Therefore, because of the local deviation of the actual tissue composition from the assumed average tissue composition, the microcalcification image c1(x,y) obtained through the first-order approximation is composed of two images. One is the true microcalcification image c(x,y) and the other image is produced by local deviation of the tissue composition from the assumed average composition.

The exact signal intensity of the superimposed image is $R_{sc}\Box\delta s(x,y)$. Generally speaking, such superimposed images due to the existence of a third material cannot be separated by using the dual-energy method. However, based on utilizing some specific conditions for the region of interest, the present invention provides approximation methods for removing the effects of the third material $R_{sc}\Box\delta s(x,y)$ on the true third material image c(x,y).

For separating the third material effects on the microcalcification image, two characteristic feature differences between the image $R_{sc}\Box\delta s(x,y)$ and that of image c(x,y) are utilized: (a) the local deviation of soft tissue composition from the average composition $R_{sc}\Box\delta s(x,y)$ has a smooth spatial distribution, in a way similar to that of the soft tissue spatial distribution sa(x,y), while the microcalcification image has an abrupt intensity change at certain small regions; and (b) the amplitude of deviation image $R_{sc}\Box\delta s(x,y)$ is small, because, as mentioned above, $R_{sc}$ is small.

Figure 6:
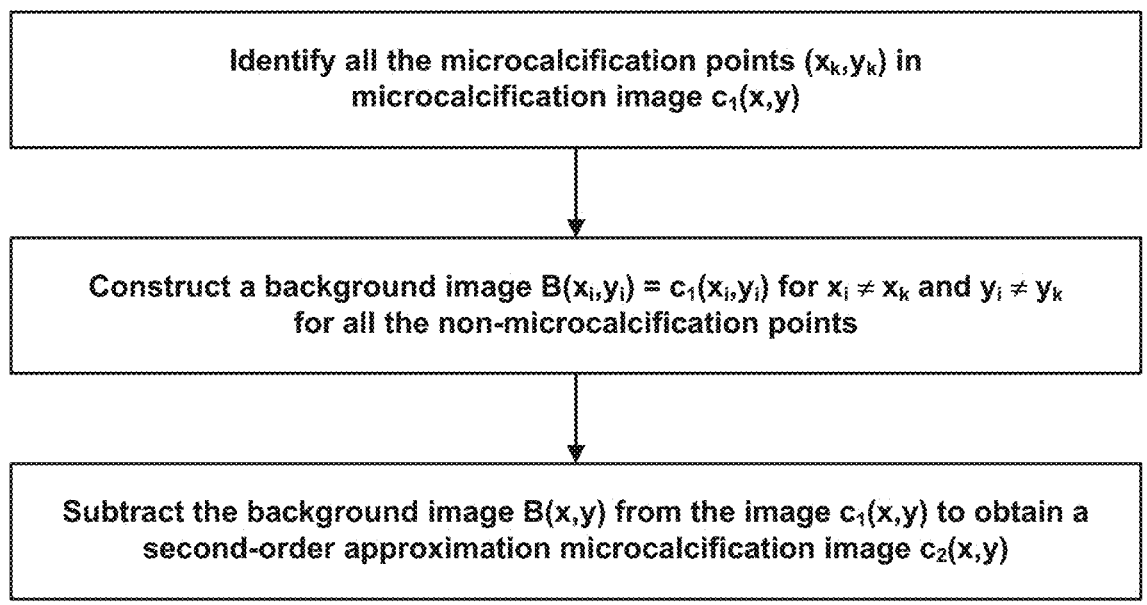
FIG. 6 is a flow diagram of the method for obtaining a second-order-approximation microcalcification image.

FIG. 6 and the following describe the procedure for obtaining a pure third material image, for example, microcalcification, at an accuracy level of the second-order approximation from the second decomposition.

(1) In the microcalcification image $c_1(x,y)$, first identify all the microcalcification points $(x_k,y_k)$. The microcalcification points are prominently different from other image points because the microcalcification image $c_1(x,y)$ is composed essentially of high-intensity isolated image points presented on a smoothly changing background. The microcalcification points are identified by pixels with a sudden intensity change at isolated points. Sometimes, microcalcification can take the form of clusters, so the points are not always individually isolated. The present invention contemplates that such clusters containing a small number of microcalcification points with a signal intensity much higher than those of adjacent points exist.

(2) Construct a background image B(x,y) for $c_1(x,y)$ from pixels $(x_i,y_i)\Box(x_k,y_k)$. That is, background image $B(x_i,y_i)=c_1(x_i,y_i)$ for $x_i\Box x_k$ and $y_i\Box y_k$ for all the non-microcalcification points. The signals in $B(x_i,y_i)$ have excluded the microcalcification points, so they must be produced by local tissue composition deviation, hence are microcalcification background signals.

(3) In the background image B(x,y) for those pixels $(x_k,y_k)$ that have been identified as microcalcification points, the signal intensity is assumed to be equal to an averaged signal intensity value interpolated from the signal intensity of the surrounding pixels. That is, $$B(x_k,y_k)=\text{averaged}[c_1(x_j,y_j)] \quad (32)$$

for j around k. Because the tissue composition has a relatively smooth change in comparison with that of the microcalcification deposits, the averaged $c_1(x_j,y_j)$ will be very close to the actual tissue composition variation at the point $(x_k,y_k)$.

(4) Subtract the tissue background image B(x,y) from the first-order approximation microcalcification image $c_1(x,y)$ to obtain the second-order approximation microcalcification image $$c_2(x,y)=c_1(x,y)-B(x,y) \quad (33)$$

In the image $c_2(x,y)$, the image signal intensity should accurately represent quantitative microcalcification density without being affected by tissue composition variations.

Figure 7:
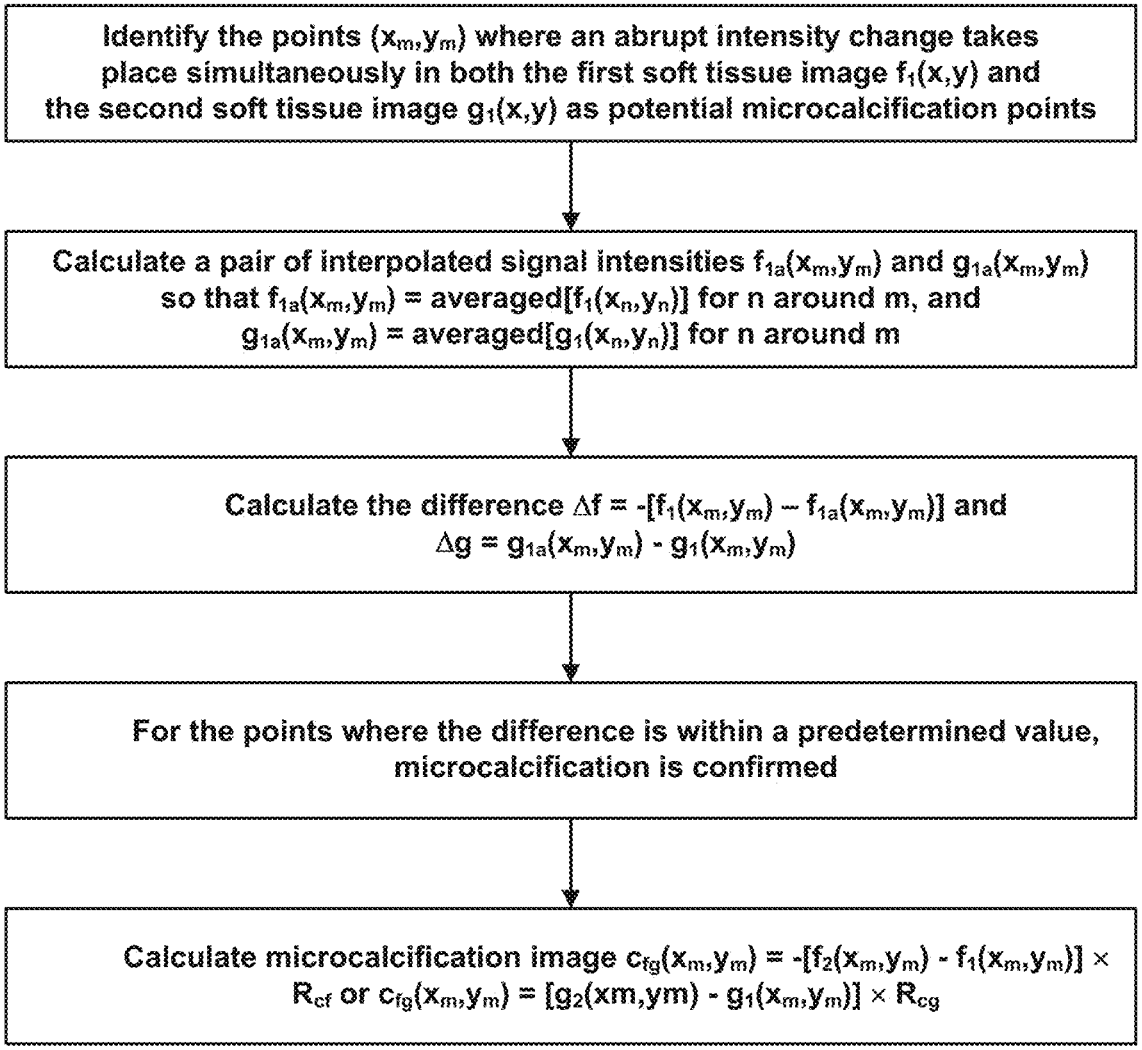
FIG. 7 is a flow diagram of the method for obtaining a microcalcification image based on the information provided by the images of two different tissues.

The steps for construction of a microcalcification image $c_{fg}(x,y)$ based on the first-order approximation fat and lean tissue images $f_1(x,y)$ and $g_1(x,y)$ are described in FIG. 7 and are as follows:

(1) Identify the points $(x_m,y_m)$ where an abrupt intensity change relative to that of adjacent points takes place simultaneously in the first soft tissue image $f_1(x,y)$ and the second soft tissue image $g_1(x,y)$. The points $(x_m,y_m)$ are suspected calcification sites as given by the tissue images $f_1(x,y)$ and $g_1(x,y)$.

(2) Verify whether the abrupt signal change at each point $(x_m,y_m)$ is consistent with that predicted. Only when the predicted signal change on the first soft tissue image $f_1(x,y)$ and the second soft tissue image $g_1(x,y)$ can both be quantitatively confirmed is the new third image, in this case, microcalcification image signal $c_{fg}(x,y)$ constructed. To do this, first calculate a pair of interpolated signal intensities $f_{1a}(x_m,y_m)$ and $g_{1a}(x_m,y_m)$, so that $f_{1a}(x_m,y_m)=\text{averaged}[f_1(x_n,y_n)]$ for n around m, and $g_{1a}(x_m,y_m)=\text{averaged}[g_1(x_n,y_n)]$ for n around m. Then calculate $$\Box f=-[f_1(x_m,y_m)\Box f_{1a}(x_m,y_m)] \quad (34)$$

and $$\Box g=g_{1a}(x_m,y_m)-g_1(x_m,y_m) \quad (35)$$

When these two quantities are close to being within a certain range, for example, between 20 to 40, the calcification at the pixel $(x_m,y_m)$ is confirmed. When $\Box f$ and $\Box g$ are not quantitatively consistent, the most probable reasons are that (a) the point selected according to the criteria of abrupt intensity change is not a calcification deposit, but actually represents some peculiar soft tissue structure, or (b) the point could contain calcification, but the signal intensity of the calcification is too low and submerged in noise. In both cases, the selected point cannot be taken as a calcification deposit, and should be excluded from the calcification image according to the information provided by the first soft tissue image $f_1(x,y)$ and the second soft tissue image $g_1(x,y)$. Thus, the calcification image $c_{fg}(x,y)$ may not be entirely identical to the calcification image $c_2(x,y)$. Even with these possible slight differences between the two calcification images obtained from different data analysis methods, both $c_2(x,y)$ and $c_{fg}(x,y)$ provide their own reference data. Both images are useful.

(3) According to the results of step (2), let $$c_{fg}(x_m,y_m)=-[f_2(x_m,y_m)-f_1(x_m,y_m)]\Box R_{cf} \quad (36)$$

or $$c_{fg}(x_m,y_m)=[g_2(x_m,y_m)-g_1(x_m,y_m)]\Box R_{cg} \quad (37)$$

Either value of equations (36) or (37) can be used as the calcification image intensity, because these values are close to each other. Choosing one as the final result is largely a matter of operator preference and depends on the operator's judgment. If a further comparison is needed, the value of equation (36) may be better than that of equation (37) because, in case, when the signal intensity of the first soft tissue has a smoother distribution than that of the second soft tissue. Consequently, the interpolated and averaged value may be more accurate.

The steps for obtaining a second-order approximation of the first soft tissue image $f_2(x,y)$ and a second-order approximation of the second soft tissue image $g_2(x,y)$ in which the microcalcification image is removed are described in FIG. 8 and are as follows:

(1) For each pixel of the second order microcalcification image $c_{fg}(x,y)$, identify those points $c_{fg}(x_o,y_o)$ whose intensity is zero and those points $c_{fg}(x_m,y_m)$ whose intensity is not zero.

(2) Construct images $f_2(x,y)$ and $g_2(x,y)$ where there are no changes between the first-order and second-order images at the zero intensity points, that is, $f_2(x_o,y_o)=f_1(x_o,y_o)$ and $g_2(x_o,y_o)=g_1(x_o,y_o)$.

(3) Set the remainder of the points $f_2(x_m,y_m)$ and $g_2(x_m,y_m)$ to the average of the signal intensity of the points in the vicinity, that is, $f_2(x_m,y_m)=\text{averaged}[f_1(x_n,y_n)]$ for n around m and $g_2(x_m,y_m)=\text{averaged}[g_1(x_n,y_n)]$ for n around m. After going over all pixels (x,y), two corrected tissue images $f_2(x,y)$ and $g_2(x,y)$ are obtained with microcalcification effects corrected.

In addition, the aforementioned methods are not limited to imaging of the lung or heart or vascular tissues, but may be used for imaging of microcalcification or calcification in other organs, for example but not limited to, the brain, gastrointestinal system, stomach, and liver. In particular, intracranial tumors contain various levels of calcification.

Patterns of calcification in pulmonary nodules (PN) may aid diagnosis of pulmonary diseases. Vascular calcification is an active and complex process that involves numerous mechanisms responsible for calcium depositions in arterial walls. They lead to an increase in arterial stiffness and in pulse wave velocity, which, in turn, increases cardiovascular disease morbidity and mortality.

Alternatively, instead of the microcalcification or calcification material, the imaging method may be applied to a DRC material, for example, a third tissue, or a modified tissue, a third component labeled with a contrast agent. Contrast agents may be nanoparticles or particles of different atomic Z than the rest in the region of interest, or particle derivatives conjugated with a molecular marker for the cell or tissue or the object of interest to be imaged or separated or quantified. Contrast agents can also be iodinated agents, barium sulfates, or derivatives of such molecules and other existing CT or x-ray labels. The third material, may also be an implant, surgical or biopsy tools which have x-ray absorption or x-ray detectable properties different from that of the background.

First and Second Order Approximation for Dual-Energy Decomposition Extended to Multiple-Energy Systems
Methods of Multiple-Energy Decomposition In order to separate even more materials or components in a subject than previous methods can achieve, imaging methods employing three or more energy levels are used in a multiple-energy system. Multiple-energy decomposition methods of the present invention are essentially an extension of those methods described in the Chao disclosures, using linearized methods or dual-energy decomposition methods. A generalized spectral imaging description is described in Handbook of Medical Imaging by J. T. Dobbins III, Image Quality Metrics for digital systems, 2000, pp 161-219 as $$D_{1\ldots n} = \Box[\Box_{0n}(E)\Box\exp(-(\Box_1(E)\Box t_1 + \Box_2(E)\Box t_2 + \Box_n(E)\Box t_n)]\Box\Box S(E)dE \quad (38)$$

where $\Box_{0n}(E)$ is the energy spectra of the x-ray source at the nth energy level En, $\Box_n(E)$ is the mass attenuation coefficient of the nth material component and is expressed in units of centimeter2/gram (cm2/g), $t_n$ is the mass density for the nth material component and is expressed in units of gram/centimeter2 (g/cm2), and S is the response function of the detector. Two conceivable ways of acquiring spectral information are to either vary the incident photon flux and energy spectra $\Box_{0n}(E)$ of the source with the incident energy level En, or to have an energy spectrum En-sensitive detector.

Due to the problem of scatter interference, spectral imaging has not been able to be implemented in 2D radiography format. As with the scatter removal, for example, as described in the dual-energy method in the Chao disclosures, and improved database and calibration methods, now extended to multiple-energy systems. As an example of implementation of the spectral imaging systems on 2D detector, such as a 2D radiograph flat panel based system, the following is an example of the spectral decomposition method, a triple energy decomposition method.

Triple Energy Decomposition Method

The subject contains three material compositions, for example, molecular labeled tissue or cells, bone, and non-labeled soft tissue, none of which can be ignored. The exact relationship between the experimentally acquired data and the quantities to be found can be expressed as a triple-energy x-ray imaging equation system composed of three nonlinear simultaneous equations:

$$D_H(x, y) = \Box[\Box_{0H}(E)\,\Box \quad (39a)$$
$$\exp(-(\Box_p(E)\,\Box\,p(x, y) + \Box_b(E)\,\Box\,b(x, y) + \Box_s(E)\,\Box\,s(x, y))]$$
$$\Box S_f(E)dE$$

$$D_M(x, y) = \Box[\Box_{0M}(E)\,\Box \quad (39b)$$
$$\exp(-(\Box_p(E)\,\Box\,p(x, y) + \Box_b(E)\,\Box\,b(x, y) + \Box_s(E)\,\Box\,s(x, y))]$$
$$\Box S_f(E)dE$$

$$D_L(x, y) = \Box[\Box_{0L}(E)\,\Box \quad (39c)$$
$$\exp(-(\Box_p(E)\,\Box\,p(x, y) + \Box_b(E)\,\Box\,b(x, y) + \Box_s(E)\,\Box\,s(x, y))]$$
$$\Box S_f(E)dE$$

where $\Box_{0H}(E)$, $\Box_{0M}(E)$, and $\Box_{0L}(E)$ are the energy spectra of the x-ray source at the high energy level H, medium energy level M, and low energy level L, respectively. The projection mass density for the first component in the region of the interest, p(x,y), the second component in the region of interest, b(x,y), and the third component, s(x,y) is the total amount of material along the x-ray projection line of the subject, and is expressed in units of gram/centimeter$^2$ (g/cm$^2$). For example, is p is for a plaster cast, in some instances, mixed with a contrast agent such as iodinated agent, b is for bone, and s is for soft tissue, $\Box_p(E)$ is the mass attenuation coefficient of plaster cast, $\Box_b(E)$ is the mass attenuation coefficient of bone, and $\Box_s(E)$ is the mass attenuation coefficient of soft tissue. The mass attenuation coefficients $\Box_p(E)$, $\Box_b(E)$, and $\Box_s(E)$ are all expressed in units of centimeter$^2$/gram (cm$^2$/g). All of these values are known, determined experimentally and well-documented. The term $[\Box_0(E)\Box\exp(-\Box_p(E)\Box p(x,y)+\Box_b(E)\Box_b(x,y)+\Box_s(E)\Box s(x,y))]$ is the energy spectrum of the primary x-rays incident on the detector after passing through the subject. $S_f(E)$ is the x-ray spectral sensitivity, the electrical signal amplitude from the detector as a function of the number of x-rays with energy E after the x-rays passing through the image subject, of the detector.

Figure 9:
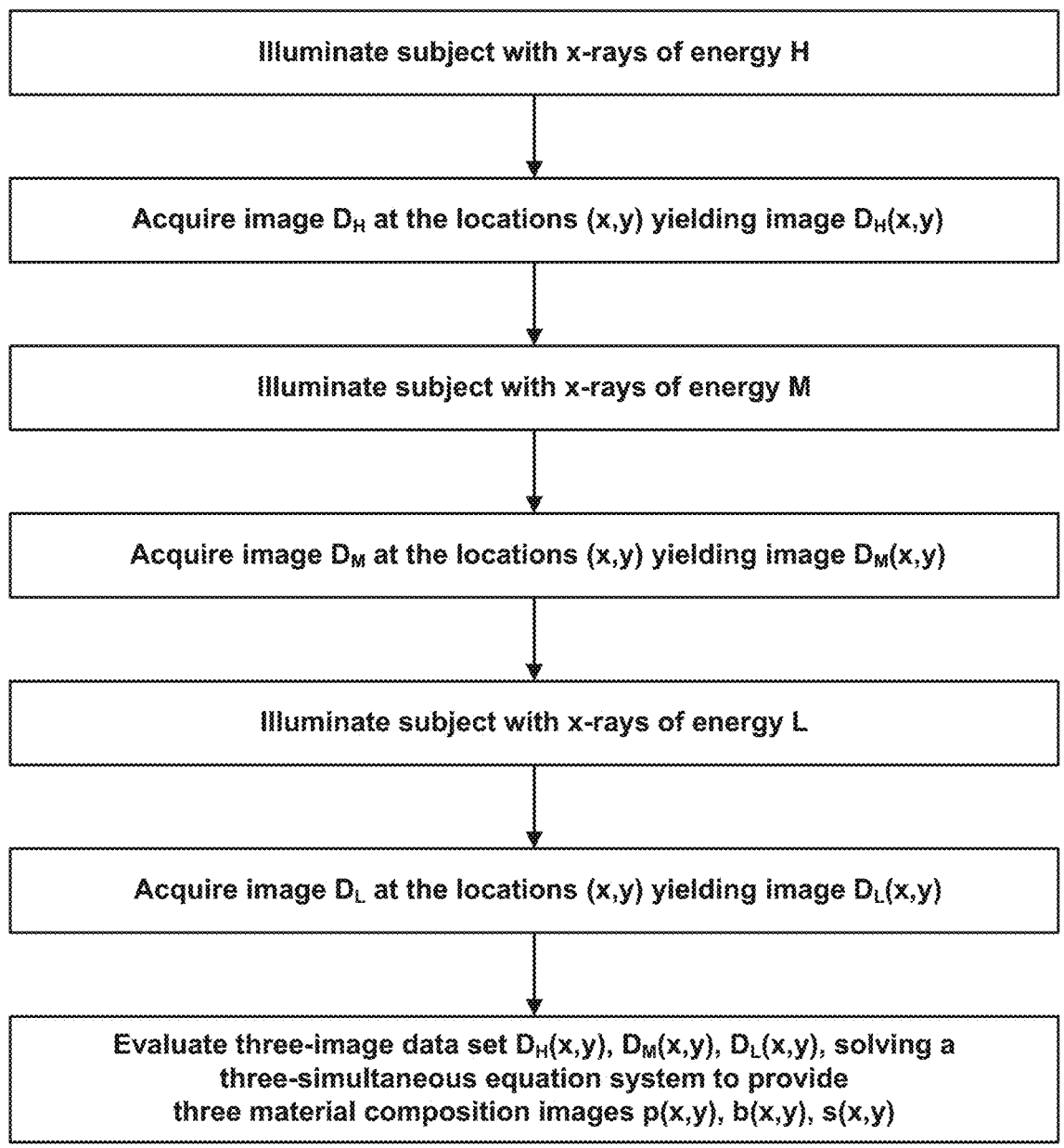
FIG. 9 is a basic flow diagram of the method for performing a triple-energy decomposition of an image.
Figure 10:
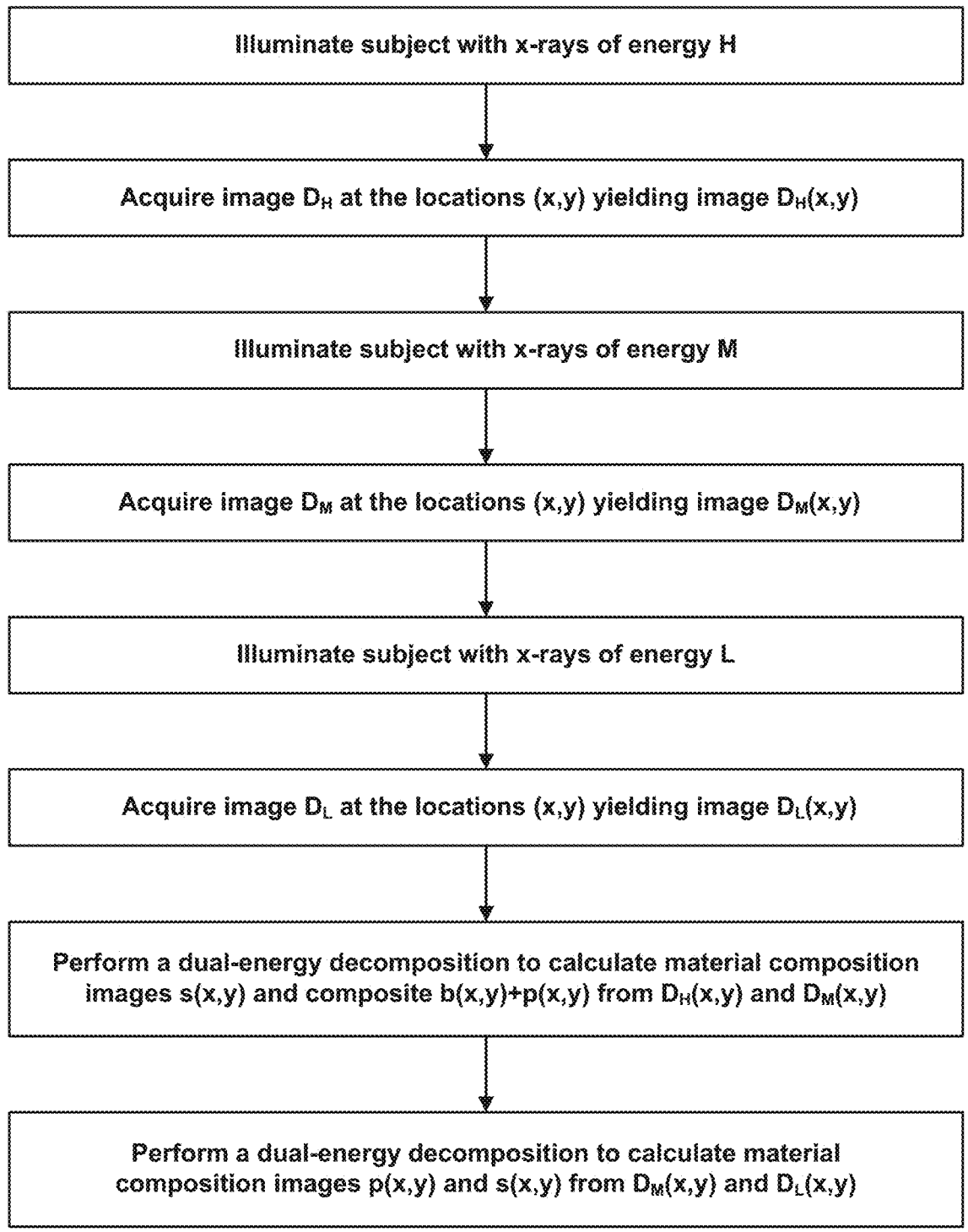
FIG. 10 is a basic flow diagram of the method for iterative dual-energy decomposition of an image.
Figure 11:
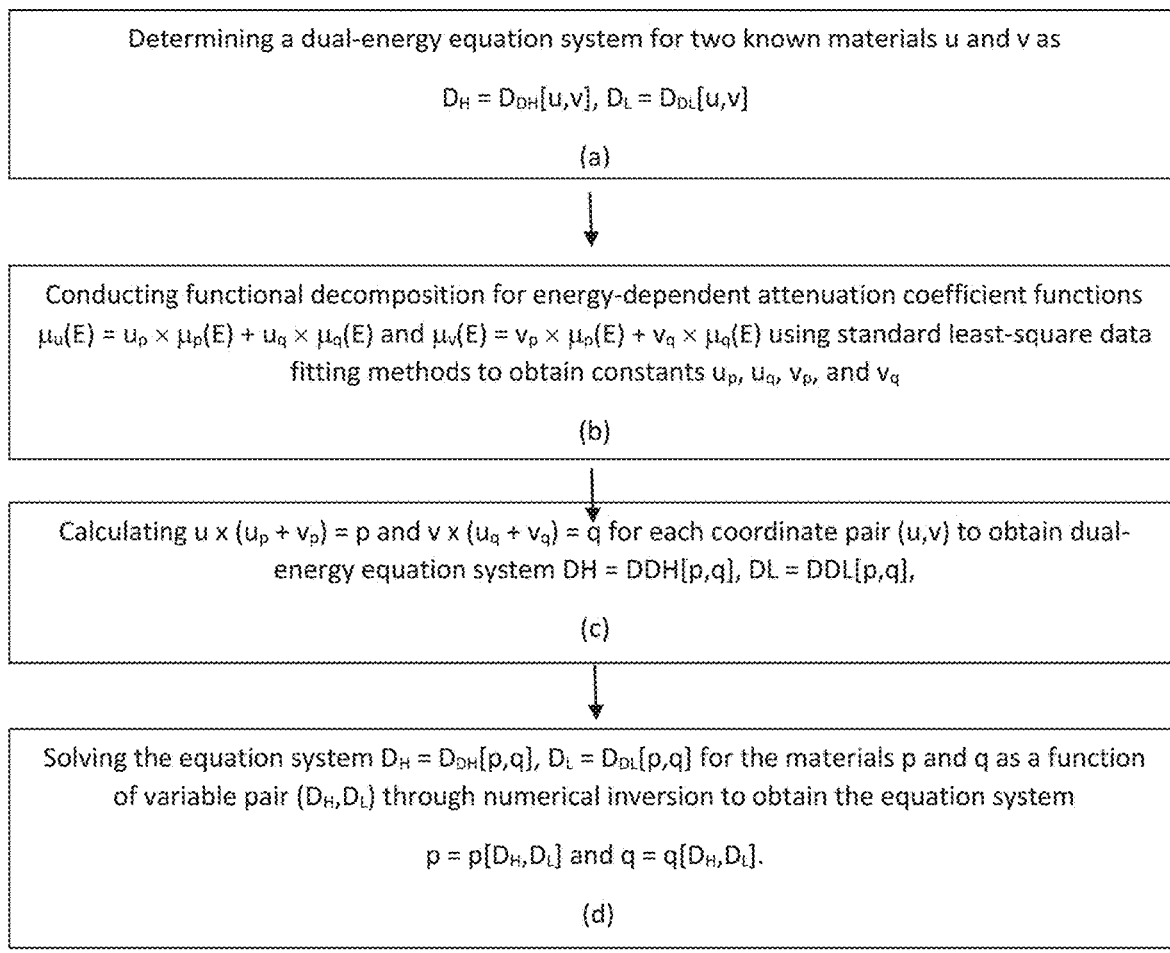
FIG. 11 is a flow diagram of the method for further correction or calibration of the fat tissue and lean tissue images.
Figure 18:
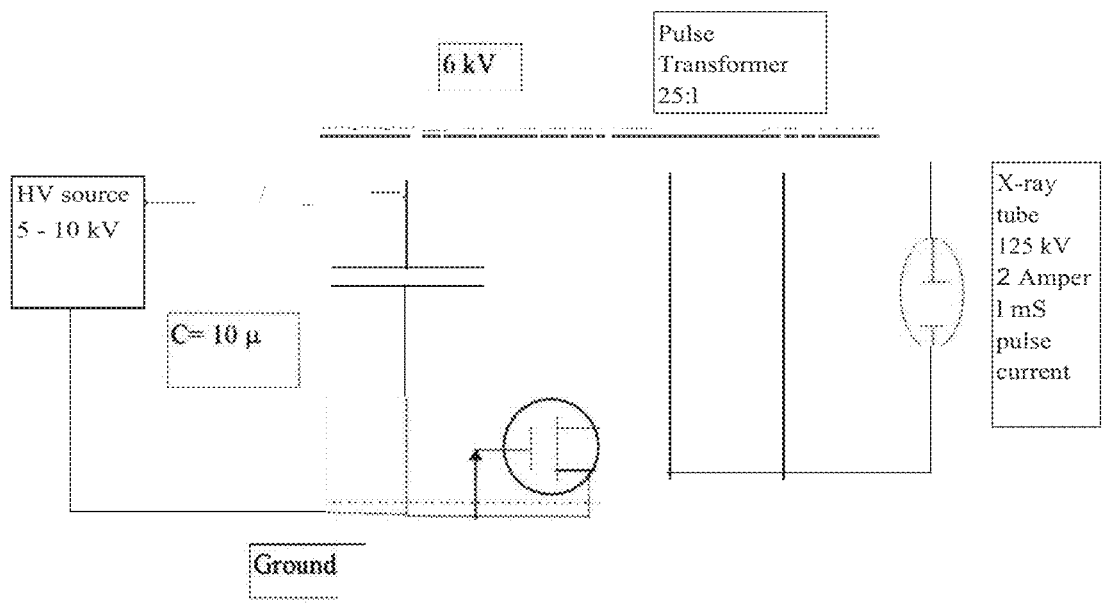
FIG. 18 illustrates a schematic of the single shot flash x-ray source.
Figure 19:
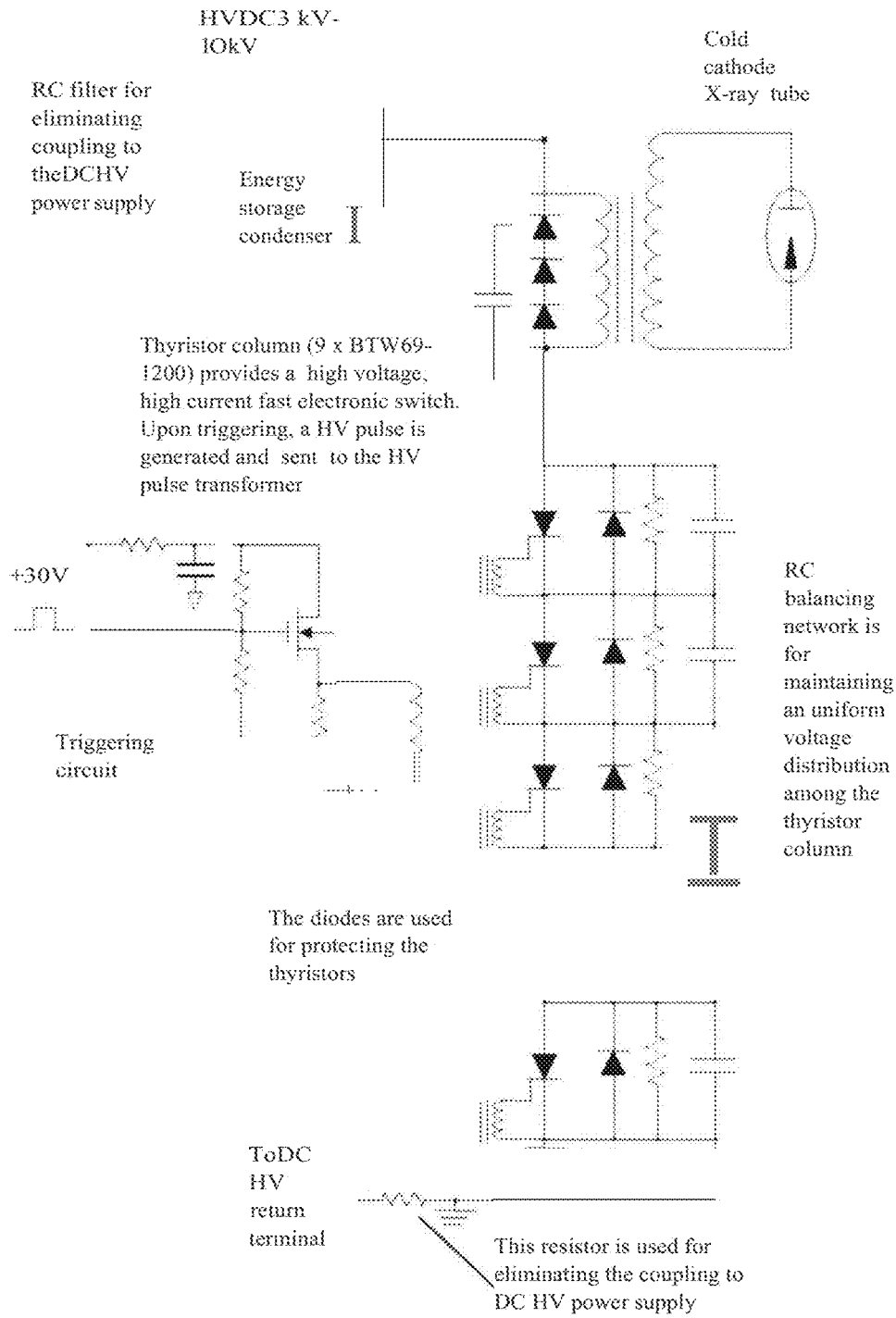
FIG. 19 illustrates electronic circuits for the flash x-ray circuits using HV semiconductor gates as switching devices.

In a triple-energy system, this equation system has three independent parameters, the density of the first component in the region of interest, $p(x,y)$, the density of the second component $b(x,y)$, and the density of the third component $s(x,y)$. The data processing method is to find the three unknown quantities $p(x,y)$, $b(x,y)$, $s(x,y)$ from the three measured quantities $D_H(x,y)$, $D_M(x,y)$, and $D_L(x,y)$ through solving the three simultaneous equations. The measured quantities $D_H(x,y)$, $D_M(x,y)$, and $D_L(x,y)$ are determined by illuminating the subject with x-rays of energy levels H, M, and L, respectively, and acquiring each image from the x-ray detector, as shown in FIG. 9.

When the subject is comprised of more than three components, more x-ray energy levels can be employed. Equation (39) is expanded by naturally adding an equation for each additional energy level and the appropriate $\mu(E)$ term to the equations for each additional component.

There are numerous ways for solving equation (39). The present invention does not limit the choice of methods for solving the equations. The following is an illustration of two methods.

(1) Linearization Method

When the image subject is not too thick, the nonlinear absorption effects of the subject can be neglected, and the nonlinear equation (39) can be linearized to give simple linear simultaneous equations:

$$\mathrm{Ln}(D_H(x,y)/\mu_{H0}) = \qquad (40\mathrm{a})$$
$$\mu_p(E_H)\,p(x,y) + \mu_b(E_H)\,b(x,y) + \mu_s(E_H)\,s(x,y)$$

$$\mathrm{Ln}(D_M(x,y)/\mu_{M0}) = \qquad (40\mathrm{b})$$
$$\mu_p(E_M)\,p(x,y) + \mu_b(E_M)\,b(x,y) + \mu_s(E_M)\,s(x,y)$$

$$\mathrm{Ln}(D_L(x,y)/\mu_{L0}) = \qquad (40\mathrm{c})$$
$$\mu_p(E_L)\,p(x,y) + \mu_b(E_L)\,b(x,y) + \mu_s(E_L)\,s(x,y)$$

where Ln( ) represents the natural logarithm of the quantity within the bracket, $D_H(x,y)$, $D_M(x,y)$, and $D_L(x,y)$ represent the signal intensity at the pixel $(x,y)$ at high, medium, and low energy, respectively, and $\mu_{H0}$, $\mu_{M0}$, and $\mu_{L0}$ represent the incident x-ray intensity at high, medium, and low energy, respectively. Since the three left-side quantities are measured raw image data (on a pixel-by-pixel basis), the three right-side unknown quantities, $p(x,y)$, $b(x,y)$, and $s(x,y)$, can be found by any standard method for solving three linear simultaneous equations on a pixel-by-pixel basis for each point $(x,y)$.

Linearization methods are easy to implement. In many cases, if the goal is to obtain distinct images for visual effects, the accuracy should be good enough. When higher accuracy quantitative results are necessary, further corrections for nonlinear effects can be made. The nonlinear correction methods for triple-energy x-ray imaging are identical with those for dual-energy cases, which are well-documented standard procedures.

In a more generalized equation to represent (40), $$\mathrm{Ln}(D_{1\ldots n}/\mu_1) = \mu_1(E_1)t_1 + \mu_2(E_2)t_2 + \mu_n(E_n)t_n \qquad (41)$$

where the equation system is solved by linearizing the system of n equations to a system of n equations and solve for material component c. In a triple-energy system, n=3, and in a four-energy, or 5-energy to n-energy system, n=4, 5, . . . n. Material decomposition of four or more components may be implemented as described without additional modification or major improvements.

(2) Multi Step Dual-Energy Decomposition Method

Due to the specific behavior of the x-ray absorption coefficients as a function of x-ray energy, for the present invention, a single triple-energy x-ray imaging operation can be taken as composed of two dual-energy imaging operations: the first step is to take the image data pair for the high energy level and medium energy level as one dual-energy decomposition process, and the second step is to take the image data pair for the medium energy level and for the low energy level as another dual-energy decomposition process. The theoretical basis for this approach is that, at the high-energy level, the x-ray interaction with matter is essentially due to Compton scattering, at the medium-energy level, it is a mixture of Compton scattering and a small portion of photoelectric absorption, and at the low-energy level, it is predominantly nonlinear photoelectric absorption. Because of this, when the two energy levels are appropriately selected within a sufficiently narrow energy range, the rule for dual-energy decomposition holds true.

In the first step, the x-ray absorption coefficient for the molecular-labeled tissue or plaster cast material can be considered to be the same as that of bone, thus a two-material system can be decomposed by using dual-energy method. As a result, the material composition of human body soft tissue on one hand and the material combination of the bone and the plaster cast material on the other can be separated by using the dual-energy decomposition method. Then, further in the second step, by using the dual-energy image data pair for the medium- and low-energy levels, the material composition of bone and molecular label or plaster cast can be decomposed.

One of the advantages of treating the triple-energy x-ray imaging decomposition as two separate dual-energy decomposition is that all currently-available results and methods for dual-energy imaging can be directly utilized.

For multiple-energy x-ray imaging decomposition with four or more energy levels, similar dual-energy decomposition steps may be adopted. For example, a single component image at one energy level, in some cases, at its absorption edge level, and the rest of the multiple components at a different energy level, and then one or multiple iterations of dual-energy decomposition for the rest of the components until an individual image of each component is derived.

Therefore, the methods of the present invention can provide functional analyses in space and time of contrast-labeled materials in the subject, as well as their positions and characteristics in space and in time, and their location relative to an organ or organ system.

Alternatively, multiple-energy system may be implemented in repeating units of a single pulse or more than one pulse, each with various energy stages. For example, repeating units of a single pulse or more than one pulse illuminating the subject, where each pulse is designed to have each of multiple energy levels to emit at different time intervals within the pulse. The detector used is energy-sensitive or is of the photon-counting type that may sample at different energy levels at different times within the pulse time interval.

AI and Deep Machine Learning and Artificial Neural Network

One component or multiple component images may be generated by a user or digital program setting one or more criteria for looking up in the aforementioned database in a material library. Each time, only a subset database is searched for decomposition purposes. Such look up process may repeat iteratively, each time with the same or different set of databases, sometimes, much smaller. Such process utilizes methods of artificial intelligence, artificial neural network, deep neural network, and convolutional neural network known to those familiar with the art.

K Edge Methods

The present invention includes a multiple-energy system, or alternatively called spectral imaging system method, which may be comprised of the energy decomposition methods described above combined with K-edge methods. For example, the multiple-energy system with n energy levels where n is equal or greater than three, may be extended by employing K-edge subtraction imaging methods. For example, a component in the region of interest has an absorption edge that is different from that of other components contained in the background image in region of interest. The K-edge subtraction method uses narrow-band x-ray spectra with energies infinitesimally below and above the K-edge energy of the component. For example, to distinguish multiple contrast-agent-labeled components, such as a diseased tissue and an anatomical marker, the K-edge method may be used together with dual- or multiple-energy decomposition methods to distinguish or visualize each of the contrast agents in the background of multiple or overlapping components or tissues.

For example, in lung imaging, microcalcification imaging, as described in the previous section, may be combined with a K-edge method where the contrast agent labels the tumor markers. In addition, the K-edge method can be applied at the K-edge of the contrast agents to further characterize the tumor region.

Further extensions of the present invention utilizing methods employing three or more energy levels combined with the aforementioned methods in DRC component imaging and K-edge imaging can be applied to cardiovascular imaging, where a multiple-energy system separates bone tissue, heart tissue, blood vessels, other soft tissues, and contrast-agent-labeled tissues. Additional components, for example, heart valves, stents, surgical tools, catheter, and biopsy needles, may be differentiated. In spine surgery, spine and bone tissues can be separated from soft tissues, labeled blood vessels, and labeled nerve tissues. The image of surgical tools can be separated from the background and positioned precisely in 2D or 3D space using methods familiar to those in the art.

Interferogram, Phase Contrast Imaging, Coherent and Partially Coherent X-Ray Imaging The present invention further includes embodiments where an interferogram method, implementation familiar to those in the art, may be measured at each energy level, combined with multiple-energy decomposition methods to improve differentiation of materials or components that otherwise look similar for example, those of low-atomic-Z materials.

Summary of Multiple-Energy Material Decomposition Mathematical Expression with Scatter Removal Multiple-energy system material decomposition may be accomplished by the linearized equation system method or by iterative dual-energy material decomposition. With the latter, all previous methods and results for dual-energy material differentiation and decomposition and scatter removal methods may be utilized. And with improved database and simulation and data synthesizing methods, the present invention provides a multiple-energy system and methods for fast and accurate material decomposition, imaging, and quantitative analysis in medical, life science and nondestructive testing applications. Thus, generally, with the ability to remove noise, scatter, spectral imaging may now be applied to 2D-detector-based radiography.

Thus it has been shown and described methods for x-ray imaging of a subject. Since certain changes may be made in the present disclosure without departing from the scope of the present invention, it is intended that all matter described in the foregoing specification and shown in the accompanying drawings be interpreted as illustrative and not in a limiting sense.

The present invention relates generally to digital x-ray imaging and, more particularly, to a method of digital imaging of an organ, or part of an organ tissue or an organ system that uses dual-energy apparatus and methods for separating a single organ x-ray image into component images, each representing a single physical substance.

The method of the present invention is to use the basic method for removal of scatter and the basic method for dual-energy x-ray imaging to first separate a mixed breast image into four basic image components: a scatter image, a lean tissue image, a fat tissue image, and a microcalcification image. "Microcalcification" is used interchangeably with "calcification". These images are a first order approximation. Then the three material compositions of the human breast are taken into account. In the second order approximation, the microcalcification image, lean tissue image, and fat tissue image are separated so that each contains only a single breast component.

The method of obtaining the first order approximations includes the steps of (a) performing a calibration, as described below, to obtain a pair of numerical relationships for the front detector at the high and low energies for the microcalcification c and the soft tissue s to obtain the functions c=c(DH,DL) and s=s(DH,DL), (b) perform a calibration to obtain a pair of numerical relationships for the front detector at the high and low energies for the fat tissue f and the lean tissue g to obtain the functions f=f(DH,DL) and g=g(DH,DL), (c) illuminating the subject with x-rays of said average energy level H and of average energy L, (d) acquiring high-resolution images DfHh(x,y) and DfLh(x,y) from the front detection locations (x,y), where the images are composed of both primary and scatter x-rays, (e) calculating a pair of high-resolution scatter x-ray images DfSHh(x,y) and DfSLh(x,y), (f) calculating a pair of high-resolution primary x-ray images DfPHh(x,y)=DfHh(x,y)−DfSHh(x,y) and DfPLh(x,y)=DfLh(x,y)−DfSLh(x,y), (g) performing a dual-energy decomposition for the image pair DfPHh(x,y) and DfPLh(x,y) using the functions c=c(DH, DL) and s=s(DH,DL) to obtain two first order approximation material composition images c1(x,y) and s1(x,y), and (h) performing a dual-energy decomposition for the image pair DfPHh(x,y) and DfPLh(x,y) using the functions f=f(DH,DL) and g=g(DH,DL) to obtain two first order approximation material composition images f1(x,y) and g1(x,y).

The method of obtaining the second order approximations corrects for microcalcification effects and includes the steps of (a) identifying all microcalcification points c1(xk,yk) and all non-microcalcification points c1(xi,yi) in the image c1(x, y), (b) constructing a back ground image B(x,y) where points B(xi,yi)=c1(xi,yi) and where points B(xk,yk) are interpolated from points c1(xj,yj) around points c1(xk,yk), (c) subtracting the background image B(x,y) from the image c1(x,y) to obtain a second order approximation microcalcification image c2(x,y), (d) identifying all zero points c2(xo, yo) and non-zero points c2(xm,ym) in the image c2(x,y); (e) constructing a second order approximation fat tissue image f2(x,y) where points f2(xo,yo)=f1(xo,yo) and where points f2(xm,ym) are interpolated from points f1(xn,yn) around points f1(xm,ym); and (f) constructing a second order approximation lean tissue image g2(x,y) where points g2(xo, yo)=g1(xo,yo) and where points g2(xm,ym) are interpolated from points g1(xn,yn) around points $g1(x_m, y_m)$.

Another object of the present invention is to provide an improved dual-energy calibration method so that the decomposed two materials are the actual breast tissue components, instead of merely equivalent materials. Currently, dual-energy calibration is performed by measuring x-ray attenuation curves using attenuation plates of a pair of different materials having known values of thickness. Generally, the materials used for calibration cannot be the same as those actually present in the human body, because the actual substances in the human body are too complex to be made as quantitative materials. For example, it is a common practice to use aluminum as a representation of human bone material and to use Lucite as a representation of human average soft tissue. Thus, the dual-energy results can only provide an equivalent aluminum quantity and an equivalent Lucite quantity in terms of x-ray attenuation in the human body. By using the standard calibration method and the equivalent decomposition, the second order approximation of the present invention cannot be achieved. Thus, the improved dual-energy calibration method is part of the present invention for a high accuracy decomposition of the human breast into pure single-component images.

The calibration method of the present invention includes the steps of (1) determining a dual-energy equation system for two known materials u and v as DH=DDH[u,v], DL=DDL[u,v], (2) conducting functional decomposition for energy-dependent attenuation coefficient functions $\mu_u(E)=u_p \times \mu_p(E)+u_q \times \mu_q(E)$ and $\mu_v(E)=v_p \times \mu_p(E)+v_q \times \mu_q(E)$ using standard least-square data fitting methods to obtain constants $u_p$, $u_q$, $v_p$, and $v_q$, (3) calculating $u \times (u_p+v_p)=p$ and $v \times (u_q+v_q)=q$ for each coordinate pair(u,v) to obtain dual-energy equation system $D_H=D_{DH}[p,q]$, $D_L=D_{DL}[p,q]$, and (4) solving the equation system $D_H=D_{DH}[p,q]$, $D_L=D_{DL}[p,q]$ for the materials p and q as a function of variable pair $(D_H, D_L)$ through numerical inversion to obtain the equation system $p=p[D_H, D_L]$ and $q=q[D_H, D_L]$. This calibration is performed for the component pair microcalcification and the soft tissue, which is an average combination of fat tissue and lean tissue, and is then performed for the component pair fat tissue and lean tissue.

Multiple-energy x ray sources are used to generate individual images of each component in the subject by using multiple energy decomposition method for 2D images described the present invention.

3D image acquisition step for multiple energy 3D image reconstruction by non rotational CT methods described in prior art In addition, such methods for separating and reconstructing images of a different atomic z material, such as microcalcification or calcification and the soft tissue composed of fat or lipid dense tissue and lean tissue, or visualizing and quantification of contrast agents labeled tissue or cell or a foreign object such as a microorganism or inorganic object or engrafted tissues or stem cells may construct images or imaging sequence in multiple dimensions both in space and in time by taking two or more x ray images in three dimensional space, such as using different detectors located at a different position or x ray sources in a different location, or simply moving 20 the same x ray source or detectors to a different positions or moving the object in 3 D space or taking a second or more images at a different time. When x ray images of the individual material of differentiating atomic z or labeled with differentiating atomic z contrast agent in the subject are derived from x ray images taken of the subject in different positions in the 3D space, resulting images of the same material may be combined to give more information about position and characterization of the subject and its individual composite material or the contrast agent labeled object in the subject in 3D space. When the x ray images are taken at varying times, for example, consecutive images of the subject are taken, each time, an image of the organ 10 and images of its individual composite material and the contrast agent labeled object are derived. By tracking the dynamic position of the selected point on the organ and its constituents and the labeled object, for example. information about location, position or function or 15 movement and motion based characteristics of the contrast agent labeled object or each individual composite material of the varying atomic z number in the organ may be compared to those of the organ or the organ system. For example, tracking the movement of engrafted stem cells or immune 20 cells, or circulating tumor cells, tissue tumor cells, migration and characteristics of tumor in 3D space and dynamics behavior of such a material or kinetics of the material or the object interacting with the organ may be obtained. Therefore this method allows for functional analysis including the movement and characteristics in space and in time of contrast labeled material or the object as well as its position and characteristics in space 5 and in time, its location and conformation relative to the organ or the organ system.

The extension of the dual energy system maybe of that of a single energy system utilizing k-edge subtraction imaging methods. If the object is to visualize and separate and visualize contrast agents or calcification or an organic or inorganic component or mixture of both which has substances of different atomic z compared to the background. The K-edge subtraction method uses narrow band x-ray spectra with energies infinitesimally below and above the contrast material K-edge energy. The A-space method uses a broad spectrum x-ray tube source and measures the transmitted spectrum with photon counting detectors with pulse height analysis. Further extension of the present invention utilizes three or multiple energy methods combined with the aforementioned methods. For example, in cardiovascular imaging, a triple energy system separate bone, soft tissue, and contrast labeled heart images, in the mean time, a $4^{th}$ component, such as implants, such as heart valve, or stent or catheter, or s surgical tool can be differentiated from the rest either using even more energy levels. Or in order to limit radiation levels, use the above methods as described for separation of microcalcifications to further separate the 4th component from the soft tissues and labeled cardiac tissues. The position of the 4th component relative to the background, bone soft tissues and cardiac tissues can be precisely determined, in some cases, can be in the um range, in 2d or multiple dimensions depending upon the detector used. Another example is the cancer tumor removal using surgical tools or radiation therapy. The precise location of the labeled cancer tissue and diseased tissues can be located compared to the background. In spine surgery, spine and bone tissues can separated from the soft tissue, labeled blood vessels and labeled nerve tissues, the image of surgical tools separated from the background and positioned precisely in the 2D or 3D space. In automated x ray inspection, multiple components can be separated using the same methods. And in characterization of materials, similar methods are used. In luggage scanning and inspection, same methods are used for separation, identification and positioning of known and unknown materials and substances.

Aforementioned claims 1, 2, 3, 4, 5, 6, 7, 8 can be applied to a second x ray image or more x ray images 34 taken of the subject with overlapping third component, such as microcalcificaiton or calcification or atomic z different material or contrast agent labeled material, or a foreign object. The image maybe taken by a different position of x ray source or a second x ray source, or different detector or second detector or simply a different position of the subject. Combined images provide more information on the position or location of the components relative to each other, especially the third material, which overlaps the background comprising of first and second or more materials whose images and density information can be separated by the multiple energy x ray system.

The relative information among all materials can be imaged overtime to analyze locations and positions of each material relative to the others. When there is one 2D image taken, relative location and position of each component can be derived. When there are multiple dimensional images, the relative position and location of each component is derived in three dimensional space.

10. Aforementioned, claim 1-8 can be applied also to when two or more x ray images of the subject are taken at different times, for example, consecutive images of the subject are taken, each time, an image of the subject and each components are derived. By tracking the position of the selected component in the subject, for example, information about location, position or dynamic movement and motion characteristics of the selected component in the subject are obtained.

11. Aforementioned claims 9 and 10 are combined to provide dynamic as well as static characteristics in 3D and in time. Relative position, characteristics in space, dynamic movement, and component interaction kinetics can be recorded and tracked. For example, in tracking of stem cells, surgical tools, implants, components in in organic subject or organic subject, a mixture of inorganic and organic subject.

12. Aforementioned claims 1-11 may be applied to systems where triple or more energy such as spectrum energy x ray sources are used. In this case, any two energies of the triple or spectrum energy x ray sources may be used for imaging, quantification and image separation as described for selected composite materials in the subject.

13. Aforementioned claims is a stationary or portable system which has power outlets, 14. Aforementioned claims is a portable system based on battery operated x ray source and detector assembly.

15. A battery operated portable systems based on published patents and provisional patents as described in U.S. Pat. Nos. 5,648,997 and 5,771,269, 6,134,297A and 6,173, 034B1, U.S. Provisional Patent Application No. 62/620,158, and No. 62/628,370 and U.S. 62/628,351

16. a battery operated or outlet powered system which is foldable in to a container, which can be carried on a should bag or rolled in a luggage roller or as in a pelican case.

17. a battery operated system which has a x ray input beam management system for the safety of field operator and or x ray shielding system for scattered x ray for the safety of the field operator, and, or patient if it is used for medical purpose.

18. a 3D portable system based on all of the above apparatus and methods by combining two or more 2D images of a subject taken by aforementioned systems, with x ray source and the subject move relative to each other, or as a conventional 3D system setup, with both x ray source and the detector move, to resolve unknown pixels in the third axis.

19. x ray source used in aforementioned claim is a monochromatic source 20. aforementioned apparatus is used with a k-edge subtraction imaging method.

21. Aforementioned apparatus and methods is in a A-space method. Where detectors are energy sensitive.

22. Aforementioned method in 1-19 is combined with K-edge subtraction imaging or A space method or both to further differentiating materials 23. aforementioned method in 1-22 are used to image inorganic subject with multiple substances 24, aforementioned method in 1-22 are used to image subjects comprised of both organic and inorganic materials.

25. A portable, carryon, foldable 2D or 3D system based on scatter and primary separation methods and dual energy and multiple energy and spectrum energy x ray source, described in U.S. Pat. Nos. 5,648,997 and 5,771,269, 6,134, 297A and 6,173,034B1, 26. A portable, carryon, foldable 2D or 3D system, as described in U.S. Provisional Patent Application No. 62/620,158, No. 62/628,370 and U.S. 62/628,351

1. The first is that the x-ray source described in the patents emits x-rays of two different energy spectrums or single energy spectrums, whereas in the present invention, the x-ray source emits x-rays of more than two-energy spectrum in certain applications in the calibration step of multiple energy x ray imaging.

2. The second difference is that, in addition to calibrate primary signal on the front detector and primary signals on the back detector by thickness of various components of varying atomic z and composition, for example, in in vivo or ex vivo imaging, more than just bone and soft tissue thickness, but additional tissues or foreign objects or components are used to calibrate, such as surgery tools or implants or contrast labels or a third component in an imaged object.

3. Third difference is that microstructure of various spatial complexity and dimensions and composition complexity which are capable of perturb x ray energy spectrum differently, for example, which are similar to those expected in the imaged subject are introduced in the calibration step for each energy level image received on the detector. It is used to correlate primary x ray signal on the front detector compared to that on the rear x ray detector at x ray wavelength and energy levels as specified in the system. In some cases, same methods are used for correlating scattered x ray from the front detector and that from the rear detector. Simplified version of such microstructures in terms of complexity and composition maybe used.

4. The forth difference is that in one embodiment, the rear detector is replaced by single or cluster of detector cells at each location of selector material of the beam selector.

5. The beam selector can be shifted and moved in three dimensions or focal point adjusted either manually or automatically with actuators and electronics control to allow flexibility of x ray source x ray emitting positions.

The term "selected location" is defined as a location on the x-ray sensitive medium of the rear detector 26 where, due to the function of the beam selector, only primary x-rays are received, and from which the scatter x-rays are substantially blocked. The "selected projection line" is defined as a straight line connecting the x-ray source 12 to a point in the "selected location". Typically, the point is close to the center of the selected location. Note that for the rear detector assembly 26 of this embodiment, only the signals at the selected locations are utilized. The rear detector cells at the selected locations have a fixed geometric relation with some of the front detector cells. This relation is established by drawing a selected projection line from the x-ray source 14 through the beam selector 18 to the selected location. This selected projection line intersects the rear detector surface at a rear detector cell at a coordinate (i,j), and intersects the front detector have a fixed geometric relation with some of the front detector cells. This relation is established by drawing a selected projection line from the x-ray source 14 through the beam selector 18 to the selected location. This selected projection line intersects the rear detector surface at a rear detector cell at a coordinate (i,j), and intersects the front detector surface at a front detector cell at a coordinate (x(i),y(j)). Here (x(i),y(j)) denote the Cartesian coordinate (x,y) of the front detector cell in the front detector assembly 16 closest to the selected projection line. An image file Drl (i,j) acquired from the rear detector assembly 26 contains only the signals at the selected locations where the primary x-rays are received, and the scatter x-rays are substantially blocked. The data at the image pixel (i,j) is the data obtained either from a single detector cell or from a combination of a small number of detector cells around the selected projection line. Similarly, Dfl (x(i),y(j)) denotes an image file from the front detector assembly 26 having a low spatial resolution. The data at the image pixel (x(i),y(j)) is the data either of a single detector cell or of a combination of a small number of detector cells around the selected projection line. The relationship between (i,j) and (x(i),y(j)) is experimentally established for all of the holes 20 of the beam selector 18 and stored.

The forth difference is that in one embodiment, the rear detector is replaced by single or cluster of detector cells at each location of selector material of the beam selector as described in provisional patents, U.S. 62/677,312, and U.S. 62/645,163

The beam selector can be shifted and moved in three dimensions or focal point adjusted either manually or automatically with actuators and electronics control to allow flexibility of x ray source x ray emitting positions. As described in US provisional patents in 62/620,158, No. 62/628,370, U.S. 62/628,351, U.S. 62/677,312, and U.S. 62/645,163

There are two preferred embodiments for using beam selector and single energy or dual or multiple energy x ray source. Both apparatus embodiments include an x-ray source, a two-dimensional front detector, a beam selector, and a two-dimensional rear detector. In general, the beam selector passes some of the x-rays to the rear detector and blocks other x-rays from the rear detector. The difference between the apparatus embodiments is in which x-rays the beam selector passes and blocks. In the first embodiment, the beam selector passes only primary x-rays to the rear detector and blocks scatter x-rays. In the second embodiment, the beam selector passes scatter only to some locations of the rear detector, blocking primary x-rays to those locations, and passes both primary x-rays and scatter to the remainder of the locations of the rear detector.

Both method embodiments include the steps of (a) illuminating the subject with x-rays from the x-ray source, (b) producing a 10 low-resolution primary x-ray image at the rear detector DrPl, (c) calculating a low-resolution primary image DfPl at the front detector along the selected projection lines, (d) producing a high-resolution image Dfh from the front detector, (e) producing a low-resolution image at the front detector Dfl from Dfh, (f) subtracting DfPl from Dfh to determine the low-resolution scatter component DfSl, (g) smoothing the low-resolution scatter component DfSl by removing the high-spatial-frequency components, (h) calculating a high-resolution scatter image DfSh by interpolation of the smoothed low-resolution scatter component DfSl, and (i) subtracting the high-resolution scatter image DfSh from the high-resolution image Dfh to yield the high-resolution primary x-ray image DfPh.

Another preferred embodiment is first and live x ray measurements of single, dual energy, three energy, each generated by one pulse with one or two or more energy profiles or two pulses, or three pulses or more pulses of various energy levels, based on what is required for the material decomposition and in some instances, scatter removal, of the target or the region of interest, or quantitative analysis of composition of not labeled or contrast agent labeled regions.

Means for Closed Loop Feedback System for Reduced X Ray Dosage

In one preferred embodiment, based on the first image or the first set of first images acquired for the target in the region of interest, or the first image of the region of interest or first images at dual or multiple energy level, the x ray beam radiation output level on the region of interest is adjusted and x ray beam is adjusted spatially to illuminate only region of interest or the target to minimize the input x ray dosage for the subsequent first measurements and live measurements without comprising acquired data for the purpose of visualization and quantitative analysis.

Figure 8:
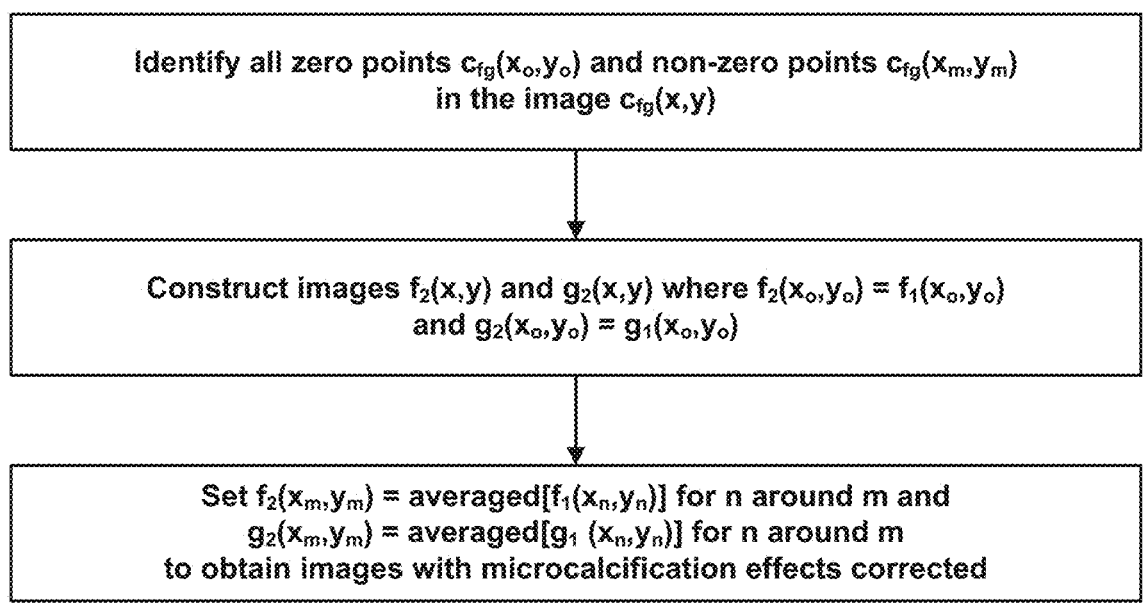
FIG. 8 is a flow diagram of the method for obtaining a second-order approximation of the first and second soft tissue images with microcalcification removed.

FIG. 8 illustrates a preferred embodiment where the collimator 10 202, with transmissive region 200 interlaced with opaque region 201.

In FIG. 8, an embodiment of the collimator 202, has transmissive region 200 interlaced with opaque region 201.

X ray beams from a x ray source maybe scanned in a preprogrammed pattern during one or multiple frame of x ray sampling. Alternatively, an X ray source can simply illuminate the entire region 202 or selective regions of 202 to produce x ray nanobeams or selectively produce x ray nanobeams.

Retrofit Kit Configuration

In a preferred embodiment, the present invention also includes retrofit hardware assemblies and software to modify existing hardware and software a user may already have—which is for example, a x ray source capable of generating x ray at the energy level pertaining to the specific application. For example Inmedicalworld, e.g. 20 KeV-1000 KeV·Inradiationtherapy,Mkev Monochromaticsource,canbeanyenergylevel,or0-70 KeV for example for synchrotron and alike sources. Or such source may have higher energy level Monochromaticsourcederivedfromconventionalxraytubes can be any of the x ray tube energy level, resulting from filtering and customization of anode target.

InUltrafastxraysource

A retrofit kit may include any one or more of the following
1. Calibration kit including both hardware and software
2. Software to calibrate for the methods described in this invention 3. One or more collimators to modified output from the x ray source beam for scatter removal or material decomposition imaging.

4. Hardware and software to modify x ray source and x ray source control to switch from different energies 5. Adding One or more x ray sources as described in this invention 6. Replacing existing x ray source with new x ray sources 7. X ray detectors assemblies as described in the scatter removal and material decomposition means in this invention, to replace film 8. Software for imaging process and or acquisition 9. Hardware positioning or mover to move x ray source or other parts of the x ray system involved in the methods described in this invention 10. Beam selector to modify existing dual or multiple layer detectors 11. Beam selector plus a detector to complete a dual detector scatter removal assembly if there is already an existing detector 12. One or more detector if there is already a beam selector or collimator and a detector.

13. A tunable hardware such as mem or crystal for beam steering or adjusting x ray beam field of view and other output properties or selecting nanobeams 14. A x ray beam position steering device or an electron beam steering device 15. If there is already an x ray source, adding one or more x ray sources or hardware to create more x ray emitting positions.

16. Any additional hardware needed for spectral absorptiometry or x ray microscopy 17. Andy additional hardware needed to include x ray or non x ray imaging modalities and technique and spectroscopy or light analysis system including x ray spectral absorptiometry, or x ray microscopy, optical spectroscopy, MRI, PET, Optical Means, Photo Acoustic, Ultrasound, Thermo imaging and analysis.

The various contrast agents are modified and linked to each other to enable sensitivities for two more imaging modalities or colocation of imaging methods such as photoacoustic imaging or PET or MM, or Optical Coherence Tomography, or bioluminescent or fluorescent imaging or ultrasound imaging. The contrast agent for each modality can be chemically linked to ensure colocation.

In addition, further modification, such as micelles or nanomicelles, or lipidified version of the molecules or any combination of such are used.

The present invention includes contrast agents which are multiple purpose can serve for flat panel and rotational MM systems and ultrasound as well as those which are used in fluorescent and optical methods such as microscopy, endoscopy and photoacoustic.

Additional aspects of the present inventions are as follows:

Other examples of naturally occurring or non toxic regents Air, gas, for example, intraosseous gas and intradiscal gas, air gap in the lung, or cation ++ rich region presence in arthritis, any x ray detectable region which are differentiable from the rest of region of interest, include those produced by enzyme activities, including aggregates of molecules in areas such as intracellular regions.

The present invention include in vivo liquid biopsy.

The present inventions include measurement of physiological state, such as Oxygenated state, change in state, such as movement, or oxygenation or previously measurable event by optical method, spectroscopy method, molecular interaction, flow dynamic and flow speed in vivo, which can trigger a change of state in vivo, which can be measured by 2D or 3D x ray quantitative method as described in the present invention.

The present invention includes the measurements of molecular, atomic, celluar and structural, or phenomina or movement or fluidic dynamics, may be triggered by internal or endogenous Chemical, electrical, electromagnetical, electrochemical, mechanical, acoustic event, magnetic or combination of two or more.

The present invention includes the measurements of molecular, atomic, celluar and structural, or phenomina or movement or fluidic dynamics, may be triggered by external force due to interaction with target or region of interest via chemical, electrical, electromagnetical, mechanical, electrochemical, magnetic, acoustic, or combination of two or more of these external force based events combined with internal events.

For example, fast events which characterizes kinetics of atomic and molecular, or nanostructure, microstructure, cellular and combinations of one or more events Contrast Agents Level For organic and non-organic objects which are not atomic Z differentiating from each other, different atomic z materials or radiolabel such as iodine maybe simply mixed in with the matter to be imaged to achieve the density required to be visualized in 2 dimensions.

The proportion of the radio labeled needed to visualize these materials will need to for example, 1) allow bone casting to solidify and achieve the rigidity and stability needed over time for the bone healing to occur and other intended function of the cast; 2) to allow quantification and visualization in x ray imaging and therefore separation of cast image from the human organ/tissue image which are bone or soft tissue.

To achieve 2), the following formula needs to be considered in evaluating of density needed in mixture for x ray detector to sense the signal needed for imaging and quantification.

X ray transparency of a substance primarily depends on density. Theoretical and experimental studies show that when an X ray beam transverse a medium, the beam intensity will be reduced due to both absorption and deflection of photons by the medium, the degree of x ray attenuation obeys the following equation:

$$I = Ioe-\mu x$$

Where I is the transmitted beam intensity, Io is the incident beam intensity, x is the thickness of the medium. The mass attenuation coefficient, $\mu$ expressed in $$\mu \rho Z4/AE3$$

Where p is the density, Z is the atomic number, A is the atomic mass, E is the x ray energy. Therefore x ray attenuation is high with low energy x rays and with materials of high atomic number.

Therefor based on this formula, For example, in bone casting material, or battery material or microchip material or Two or more 2 dimension images can be further extended to formed 2 dimension layered images, or 3 D images, the quantitative imaging data and differentiating material quantitative data, and density measurements of such materials can be derived from those of 2D data.

Another example is bone cement or casting materials or biofilms. Mixing cement and casting material with contrast agents such as iodinated or other atomic z varying label molecules or their derivatives to achieve the radio density needed for x ray detection. Or alternative inorganic compound, namely iron sulfate, silver-coated micro-particles or 1-chloronaphtalene, holium, hafnium, or even nanoparticles, other contrast agents used for in vivo imaging.

III. Methods Mixing Labels

In one embodiment, the material to be imaged is mixed with the labels which can be identified by x ray or hybrid imaging modalities.

Example: 1. Plaster Cast

Mix the contrast agents with the plaster casting evenly. The contrast agents maybe conjugated beforehand with a color to ensure homogenized mixing by visual inspection.
  Add water
  Fiber glass cast
  Mix the contrast agents with the resin evenly. The contrast agents maybe conjugated or mixed with a pigment to ensure visualized verification of homogenization
  Add the catalyst to cure the fiber glass It is another aspect of this present invention is to correlate the image and densitometry and composite analysis within a single material of the subject comprised of two or more materials using 2D flat panel detectors.

The present invention includes methods to analyze relative composition, density and image information of regions in an individual component as well as that of components relative to other components in position, density and image including morphology as well as dimensions of image such as tumor size or disease tissue size.

It is one aspect of this invention to include diagnosis of disease generally performed with quantitative aspect of conventional CT scanner in 3D format using a 2D flat panel quantitative imaging method and multiple dimension methods based on 2D flat panel quantitative imaging method using separation of tissue images, location, density measurement and dimension measurement and motion measurement of individual tissues as well as that of other materials or tissues and analysis of relative measurements of components in these parameters. Such analysis can be done over time and individually. Such as cancer diagnosis, circulatory (blood) system diseases and conditions, such as coronary artery disease (atherosclerosis), blood vessel aneurysms, and blood clots; spinal conditions; kidney and bladder stones; abscesses; inflammatory diseases, such as ulcerative colitis and sinusitis; and injuries to the head, skeletal system, and internal organs. As the current quantitative and high resolution image parallel to that of CT, details and quantitative information can be revealed by 2D flat panel image with scatter removal method and separated tissue images and quantitative measurements correlating dimension and density and images.

For example, for example, a pulmonary embolism, or blood clot in their lung, a spiral CT maybe required to see details of various tissues in order to diagnose. However, using the current method with 2D flat panel, much lower radiation is needed in order to achieve the detail and quantitative analysis information need to achieve diagnosis.

This applies to many different types of tissues—including the lungs, heart, bones, soft tissues, muscles, and blood vessels.

It is another aspect of this invention in material characterization and identification in industrial settings, where CT scanner is required, a system based on 2D flat panel maybe sufficient for quantitative analysis of presence, location, characterization and identification of a material or substance embedded in the subject in industrial applications such as cargo inspection, security x ray and automated x ray inspection.

The present invention relates generally to digital x-ray imaging and, more particularly, relates digital x-ray imaging using 2D flat panel for a combined quantitative and image analysis of individual materials in a subject, in time and space, some functions are to replace the usage of conventional CT scanner It is another embodiment of this invention to collocate with PET or Optical Imaging, or MRI or Ultrasound or Acoustic or Photoacoustic Imaging method.

It is one aspect of this invention to include X Ray Particle Image Velocimetry, to measure flow using particles for example, microbubbles as the tracer particle for investigation of hemodynamic characteristics and circulatory vascular diseases. This invention is especially useful for deep tissue liquid flow measurement as the overlapping tissues and scatter reduces the visibility and quantification capabilities of 2D x ray detector based method.

Stereoscopic PIV utilizes two detectors with separate view angles to exact z axis displacement. Or a three dimensional acquisition of 2D flat panel based imaging method, which is fast in acquiring multiple dimension representation, can be fast enough to acquire velocity in three dimensional space.

Holographic PIV is also part of the present invention using interferogram based method to II. Method 1. A single, dual and triple-energy or multiple x-ray imaging system based on 2d flat panel for taking one or more two-dimensional images of a subject from a different location and, or at different times, said system comprising:

(a) in physical sequence from front to back, an x-ray source, a two-dimensional x-ray detector, said subject being a body, or a subject or region of interest of an subject, located between said x-ray source and said x-ray detector;

(b) said x-ray source being adapted to emit x-rays with three different energy spectra for passage through said subject;

(c) said two-dimensional x-ray detector receiving said x-rays from the x-ray source and converts the image information contained in the transmitted x-rays into electric signals to be sent to a computer;

2. A variation of embodiment is adding to the hardware to, the mover to move the x ray source relative to the subject, so that 2D images can be taken at different angles and combined.

3. Another embodiment of the hardware, along with #1, is the addition of a mover to move the x ray source as well as the detector relative to the subject.

4. Another embodiment, along with hardware in #1, is the voluntary movement of the subject, if it is a live organism or animal, or internal robotics of the subject to move one or more components or the entirety of the subject.

5. It is another embodiment of this invention to collocate with PET or Optical Imaging, or MRI or Ultrasound or Acoustic or Photoacoustic Imaging method.

6. The x-ray imaging system of claim 1 wherein one of said energy spectra has an average energy in the range of from approximately 15 keV to 200 KeV;

7. The x-ray imaging system of claim 1 the subject is a body;

4. The x ray imaging system of #1 the subject is in organic material or a mixture of organic and in organic material.

8. The x-ray imaging system of #1 wherein images of individual component inside the subject are separated, analyzed based on dimension, composition, thickness, shape, morphology, relative position to the rest of the subject and density, and relative movement, relative position, in time and space based on apparatus and methods described in patents a. Apparatus and method for removing scatter from an x-ray image using two-dimensional detectors and a single-energy spectrum x-ray source, U.S. Pat. No. 6,134,297 b. Apparatus and method for dual-energy x-ray imaging: U.S. Pat. No. 6,052,433 c. Apparatus and method for dual-energy x-ray imaging: U.S. Pat. No. 6,052,433 d. Apparatus and method for removing scatter from an x-ray image: U.S. Pat. No. 5,771,269 e. Apparatus and method for removing scatter from an x-ray image: U.S. Pat. No. 5,648,997 f. U.S. provisional application No. 62/692,675, 3D 3E, Calibration; 62/620,158, 62/628,370, 62/628,351, 62/677, 312, 62/700,157, 62/711,522, 62/697,174, 62/620,158 and 62/645,163—provisional patent applications filed by Zhao, on the topic of scatter removal, dual energy, triple energy and multiple energy, multiple dimension, molecular imaging and contrast agents and methods and 3D x ray imaging.

9. The x-ray imaging system of #1 wherein images and quantitative measurements of individual component inside the subject can be separated, analyzed based on parameters such as dimension, composition, thickness, microstructure, shape, morphology; one or more areas of the same component, its or their relative position, location and aforementioned parameter measurements, stand alone, and, or compared to the rest of the subject, and its relative location, position and aforementioned parameter measurements to other area or areas of the same component including density, and relative movement, relative position, dimension, composition, thickness, shape, morphology, microstructure, addition or loss of content, in high resolution and in real time, and or between time period and or in 2D and multiple dimensional space 10. The results maybe used for diagnosis of various diseases, for example dimension of vascular features, presence of clots, irregularities, microcalcifications, special substances or cysts, fractures, increase of density within a region, loss of tissue content, addition of tissue fragments, specific microstructure, derivation of composition and changes due to density measurement and images, especially in cases where high resolution and accuracies and quantification measurements are required, for example, a CT scanner, bone scanner, MM and densitometer would have to be used together or individually, to achieve results needed, or in some cases, not sufficient enough to give satisfactory answers for a relatively definitive deterministic conclusion.

11. The results are used for surgical guidance, especially for minimum invasive surgeries, radiation therapy and biopsy, especially in cases where normally a CT scanner, bone scanner, Mill and densitometer would have to be used together or independently.

12. The results are used for industrial use in identification and characterization of components, materials, substances failure analysis, parts inspections, especially in cases where normally a CT scanner would have to be used.

13. such a system can be portable 14. such a system can be battery operated 15. such a system can be portable in the field setting and can be packaged into a carryon bag.

16. such a system is portable and can be packaged into a package size of a pelican case.

17. Interferogram of scattered and primary x rays based on the above hardware and adding a diffraction grating or beam splitting after x ray source and before the subject are used in measurement of velocity of blood and other biofluid in diagnosis of diseases.

18. Particle Image Velocity Measurement based on X ray is combined with separation of tissues and measurement in time for velocity measurements.

19. Using the above described hardware and methods, relative density and images of area of interest within a first component compared to the rest of the component, and relative density and image of a different component in the area of interest adjacent or relevant to that of the first component may form indicative information for disease diagnosis or material or composition characterization or identification. And monitoring of such information in time, may be efficient in early diagnosis of diseases. Examples of diseases which can use quantitative 2D Flat panel x ray system to replace CT Scanners are:

stress fracture, the callus formation may happen near the fracture, affecting both bone measurement as well as tissue surrounding it.

Shine splint, there is a density variation atypical in the area of injury compared normal bone density and its uniformity in un affected bone areas and health tissue.

Vascular Calcification

The present invention with scatter free 2D flat panel imaging method replace neurological CT scans are used to diagnose and monitor disease condition and therapeutic response of the brain and spine. It detects bone and vascular irregularities, certain brain tumors and cysts, herniated discs, epilepsy, encephalitis, spinal stenosis (narrowing of the spinal canal), a blood clot or intracranial bleeding in patients with stroke, brain damage from head injury, and other disorders. Many neurological disorders share certain characteristics and a CT scan can aid in proper diagnosis by differentiating the area of the brain affected by the disorder, 2D flat panel based quantitative imaging as described in patent and provisional patents can now replace that.

Diagnosis and treatment and long term monitoring in Pain Management

Muscle disorders

Pinpoint the location of tumor, infection or blood clot, bleed in the brain.

Guide procedures such as surgery, biopsy and radiation therapy.

Localization of suspended cancer cells, stem cells, rare cells and foreign objects.

Treatment and surgical Planning and guidance and therapeutic and treatment response and post treatment monitoring of other organs, kidney, limbs, eyes (implant placement) in the body.

20. It is one aspect of this invention to enable material characterization and identification in industrial settings, where CT scanner is required, a system based on 2D flat panel maybe sufficient for quantitative analysis of presence, location, characterization and identification of a material or substance embedded in the subject in industrial applications such as cargo inspection, security x ray and automated x ray inspection.

21. It is one aspect of this invention to enable measurements of fluid flow characterization and identification and velocity in 2D or 3D space in industrial settings, where conventional CT scanner of prior art, optical, acoustic systems are required or any other available system and methods have not been effective and deterministic.

The present invention is a compact pulsed x-ray source giving a single-shot x-ray pulse having an x-ray output corresponding to a stored electric energy between 100 Joules and 1,000 Joules per pulse, and a typical pulse duration between 0.1 ms and 10 ms. Such an x-ray source is light weight, compact, and requires very low power supply. Suitable for human body imaging.

(3a) using a vacuum-sealed field emission tube. This is a cold cathode x-ray tube. Using cold cathode x-ray tube can significantly improve energy utilization efficiency. We note that the total electric energy required for providing a pulsed x-rays for use in producing a frame of x-ray image, is not large. For example, an average electric energy of about 500 J is sufficient. To give 500 J electric energy, is equivalent to turn on a 100 W bulb for 5 seconds. However, when a heated cathode x-ray tube is used, at least 10 times of this amount of energy is needed, because the energy utilization efficiency is low. When using cold cathode tube, the energy utilization efficiency of 50% to 70% could be achieved.

(3b) the electric energy for a single pulse operation is first stored in a condenser. The condenser is built at a pre-stage working at a much lower voltage. The voltage of the condenser is chosen to be as low as between 5 kV and 10 kV;

(3c) the electric energy stored in the condenser is delivered to the x-ray tube through a high voltage pulse transformer to provide a 100 kV to 150 kV voltage pulse.

(3d) the pulse duration is controlled to be between 0.1 ms and 10 ms. Correspondingly the current flowing in the tube will be between 10 A and 1 A to provide the desired amount of energy for a quality x-ray imaging. The pulse width and the current is determined by the parameters of the capacitance of the condenser, the inductance of the pulse transformer, and the V-1 characteristic curves of the tube. The pulsed electric current flowing in the xray tube is substantially lower than that for the nanosecond flash x-rays, where electric current is in 1,000 A to 100,000 A. The reduced electric current is very favorable for enhancing other performance parameters, such as focus size, tube service lifetime, etc.

In one embodiment of the invention, flash x-ray source is based on use of a field emission tube driven by a HV transistor-triggered pulse transformer.

In conclusion, the present invention includes an x ray source comprised of major components with typical parameters: include a 2.5 kV DC power supply, an high voltage condenser with a capacitance of 2 μF, an electronic triggering circuit, a high voltage pulse transformer encapsulated in Sylgard Silicone, and an x-ray tube contained in a plastic case. The total energy stored in the condenser for generating a single x-ray pulse was 30 J when HV=50 kV. The dimension of the whole x-ray source is about 8"×8"×16", with a weight of about 30 lb.

1. Substantially reduced size and weight. Currently the best x-ray source with heated cathodes with an output corresponding to an electric energy of 100 J per 1 second (10 mA, 125 kV) is about 100 lb. A pulsed x-ray source based on cold cathode with an output corresponding to an electric energy of 100 J per pulse will be only 30 lb. suitable for animal study. A pulsed x-ray source with 500 J per pulse will be about 50 lb. suitable for human body imaging 2. Substantially reduced power supply. To convert 100 J or 500 J of electric energy into an x-ray pulse, a heated x-ray source usually requires 50 times to 100 times additional electric energy to support system operation (for heating filaments, for maintaining a 100 kV high voltage DC power supply operation, and for tube cooling). To convert the same amount of energy into x-rays by using field emission tubes, the energy required for supporting system operation is only 1.5 times, that is total 150 J or 750 J of electric energy (for charging the HV condenser at 5 kV to 10 kV). This is very favorable for portable unit using battery as power supply.

Apparatus and method for performing triple-energy x-ray imaging for separating three materials of different atomic z number in cases of 1. Visualizing blood vessel/nerve tissues, separately from bone and other software tissues in surgical guidance or separating tissues or diseased tissues or tumors which are labeled with antibodies conjugated with various atomic z number particles or removing overlapping effects due to the presence of plaster cast in human body x-ray imaging. The apparatus consists of, in physical order, an x-ray source and a two-dimensional x-ray detector. The subject is an object composed of three or more composite with various atomic z numbers, for example, an human body organ containing molecular labels specific to tissues or diseased tissues or a human body structure overlapped by plaster cast material for medical purposes. The subject located between the x-ray source and the x-ray detector. Using a triple-energy data decomposition method, three material composition images including bone mass density image $b(x,y)$, soft tissue image $s(x,y)$ and a plaster cast mass density image $p(x,y)$ or molecular labeled tissue mass density image $p(x,y)$ can be obtained.

The present invention provides methods and apparatus for separating a human body organ image from the overlap effects caused by a plaster cast. The image subject is a human body organ or structure with certain overlapping plaster cast support. The separated images contain complete information for a separated bone image, a separated soft tissue image, and a separated image of the overlapping plaster cast; the last one is generally discarded. Thus the present invention is a triple-energy x-ray imaging. The system acquires 3 x-ray images at 3 different x-ray energy states and, after subsequent data processing procedures, provides 3 separate material composition images as described above. Another notable aspect of the present invention is to use slightly modified plaster cast materials. Currently available plaster cast uses a well-standardized material which is largely composed of calcium sulfate ($CaSO_4$) with various hydrate forms. This plaster cast material has a number of excellent chemical, physical, and mechanical attributes for use as a medical device evolving human body support. However, such classical plaster cast material has a weakness in terms of new needs for exploiting the capabilities of digital x-ray imaging. The x-ray absorption coefficient of the classic plaster cast material is too close to that of bones which is also largely composed of calcium compound. An undesirable consequence is the situation that if a high quality separated human body image is to be obtained, the corresponding imaging system has to be built with a high accuracy. To avoid the problem, the present invention advocates use of a newly created digital-x-ray-compliant plaster cast materials. A digital-x-ray-compliant plaster cast material possesses all the salient chemical, physical and mechanical attributes as those for the standard plaster cast material except that its average atomic number Z is much different. The fabrication of the digital-x-ray-compliant plaster cast material is described briefly below. A typical digital-x-ray-compliant plaster cast material can be a mixture of two materials: predominantly conventional plaster cast material with addition of a small portion of barium sulfate ($BaSO_4$). The present invention does not exclude use of conventional plaster cast material, however, if the new plaster cast is made of digital-x-ray-compliant plaster cast material, then the separation of plaster cast and the human body images can be performed very efficiently, and economically.

What is claimed is:

1. A system which images a subject, the system comprising:
    an x-ray source configured to illuminate a subject, with x-rays having at least two different energy levels;
    an x-ray measuring device having at least one two dimensional detector and configured such that a subject can be located between the x-ray source and the x-ray measuring device, the x-ray measuring device further configured to detect the x-rays after the x-rays have passed through the subject;
    wherein the x-ray measuring device is configured to reduce an effect of x-ray scatter from the detected x-rays to produce at least one image, and
    wherein the x-ray measuring device is further configured to perform a pre-measurement calibration, the calibration being performed using each material component and composites of each material component of various thicknesses.

2. The system of claim 1, wherein the x-ray measuring device is further configured to identify or quantify at least one substance in the at least one image.

3. The system of claim 2, wherein the x-ray measuring device is further configured to identify a plurality of different substances in the at least one image.

4. The system of claim 2, wherein the x-ray measuring device is further configured to identify a substance in the at least one image indicative of an abnormal condition, a disease state, and/or at least one variation in its state.

5. The system of claim 2, wherein the x-ray measuring device is further configured to identify the substance using a database, the database comprising at least one of tested or established algorithmic relationships between known materials similar to the substance.

6. The system of claim 5, wherein the database includes one or more of a physical, chemical, electrical, physiological or dynamic properties, at least of one stage of a dynamic process or movement of the known material in static, temporal, or spatial forms.

7. The system of claim 6, wherein the properties include one or more of atomic z numbers, densities, unstructured molecules, structured molecules, composite molecules, microstructures, structures, characteristic regions of a regions of interest with at least one marker in a physical, chemical, spatial, temporal or physiological form.

8. The system of claim 6, wherein the known materials are one or more tissue regions, contrast-labeled plaster cast, a material and cavity form, one or more regions of an organ, molecular complexes, contrast-labeled molecular complexes, contrast-labeled organelles, ion mixtures, an ablated region of a tissue, tumor, a diseased region of a tissue, a chemical compound, semiconductor component, metal part, an inorganic or organic substance and/or a mixture of an inorganic and organic substance.

9. The system of claim 2, wherein the x-ray measuring device is further to use a dual-energy decomposition and/or linear method for decomposition to produce the at least one image and/or to identify the at least one substance.

10. The system of claim 2, further comprising a database at each energy level for each material component and each combination of the material components with two or more components, with derived measurements without scatter interference, and wherein the x-ray measuring device is configured to use the database to identify or quantify the at least one substance.

11. The system of claim 10, wherein the system is configured to identify and determine at least one of properties or characteristics of the at least one substance by measurements using the x-ray measuring device and/or using simulated, synthesized, and/or predefined data.

12. The system of claim 11, wherein a quantitative relationship between a measurement of a known material and the substance to be measured relates to one or more of a density, atomic z, or a thickness of the respective material and substance where the known material and the substance have similar attenuation properties of x-rays.

13. The system of claim 2, wherein the x-ray measuring device is further configured to solve nonlinear dual- or multiple-energy equations to produce the at least one image, or to identify or quantify the at least one substance, or both.

14. The system of claim 13, wherein the x-ray measuring device is further configured to solve the nonlinear energy equations through numerical inversion of a multiple energy response equations system.

15. The system of claim 2, wherein the x-ray measuring device is further configured to identify the at least one substance using one or more databases, wherein the one or more databases comprise a database of known materials, a database of materials that are the same or similar to the substance, a database of measured data from known materials which have established a quantitative relationship with unknown materials based on measurements, a database of simulated or synthesized data, and/or a database of empirical data.

16. The system of claim 15, wherein the x-ray measuring device is further configured to use the one or more databases to derive a quantitative relationship between physical properties, thickness, and/or characteristics of the known material and that at least one substance, the relationship based on measured data of both the at least one substance and the known material.

17. The system of claim 15, wherein the x-ray measuring device is further configured to establish physical properties of the at least one substance using measurements by the x-ray measuring device or characterization using the simulated or synthesized data.

18. The system of claim 2, wherein the substance is a Distinct and Rare Component (DRC) material and the x-ray measuring device is further configured to perform a second order approximation and a second decomposition.

19. The system of claim 18, wherein the DRC material is tissue, modified tissue, calcification, microcalcification, and/or a contrast agent marked substance, surgical tool, biopsy tool, and/or implant.

20. The system of claim 1, wherein the subject comprises three or more different material components, four or more different material components or five or more different material components.

21. The system of claim 1, wherein a number of energy levels (n) is equal to or greater than a number of materials to be decomposed and/or identified.

22. The system of claim 1, wherein the x-ray measuring device is further configured to reduce the effect of x-ray scatter from the detected x-rays using interpolation.

23. The system of claim 1, wherein the x-ray source is configured to illuminate the subject with broad-spectrum x-rays and the x-ray measuring device is further configured to measure the received x-rays using energy-sensitive or photon-counting methods.

24. The system of claim 1, wherein the x-ray measuring device is further configured perform the pre-measurement calibration for scatter removal.

25. The system of claim 1, wherein the at least one image is produced by referencing a database of stored sinogram CT, CT, MM, SPECT, PET, spectroscopy, photoacoustic and other energy, chemical and/or electrochemical measurements.

26. The system of claim 1, wherein the at least one two dimensional detector is a flat panel detector.

27. The system of claim 1, wherein the at least one image comprises images of individual component inside the subject, the images being separated and analyzed based on dimension, composition, thickness, shape, morphology, relative position to the rest of the subject and density, and relative movement, relative position, in time and space.

28. A system which images a subject, the system comprising:
an x-ray source configured to illuminate a subject, with x-rays having at least two different energy levels;
an x-ray measuring device having at least one two dimensional detector and configured such that a subject can be located between the x-ray source and the x-ray measuring device, the x-ray measuring device further configured to detect the x-rays after the x-rays have passed through the subject, wherein the x-ray measuring device is configured to reduce an effect of x-ray scatter from the detected x-rays to produce at least one image and to identify at least one substance in the at least one image; and
a database at each energy level for each material component and each combination of the material components with two or more components, with derived measurements without scatter interference, wherein x-ray measuring device is further configured to use the database to identify or quantify the at least one substance.

29. The system of claim 28, wherein the x-ray measuring device is further configured to identify a plurality of different substances in the image.

30. The system of claim 29, wherein the x-ray measuring device is further configured to solve nonlinear dual- or multiple-energy equations to produce the at least one image, or to identify or quantify the at least one substance, or both.

31. The system of claim 30, wherein the x-ray measuring device is further configured to solve the nonlinear energy equations through numerical inversion of a multiple energy response equations system.

32. The system of claim 28, wherein the x-ray measuring device is further configured to identify a substance in the at least one image indicative of an abnormal condition, a disease state, and/or at least one variation in its state.

33. The system of claim 28, wherein the substance is a microcalcification, cancer, a tumor, a contrast agent indicative of a tumor, nanoparticles, an iodinated blood vessel and/or a contrast agent indicative of tissue.

34. The system of claim 28, wherein the database further comprises at least one of tested or established algorithmic relationships between known materials similar to the substance.

35. The system of claim 34, wherein the database further comprises one or more of a physical, chemical, electrical, physiological or dynamic properties, at least of one stage of a dynamic process or movement of the known materials in static, temporal, or spatial forms.

36. The system of claim 35, wherein the properties comprise one or more of atomic z numbers, densities, unstructured molecules, structured molecules, composite molecules, microstructures, structures, characteristic regions of a regions of interest with at least one marker in a physical, chemical, spatial, temporal or physiological form.

37. The system of claim 35, wherein the known materials are one or more tissue regions, contrast-labeled plaster cast, a material and cavity form, one or more regions of an organ, molecular complexes, contrast-labeled molecular complexes, contrast-labeled organelles, ion mixtures, an ablated region of a tissue, tumor, a diseased region of a tissue, a chemical compound, semiconductor component, metal part, an inorganic or organic substance and/or a mixture of an inorganic and organic substance.

38. The system of claim 28, wherein the subject comprises three or more different material components, four or more different material components or five or more different material components.

39. The system of claim 28, wherein a number of energy levels (n) is equal to or greater than a number of materials to be decomposed and/or identified.

40. The system of claim 28, wherein the x-ray measuring device is further configured to reduce the effect of x-ray scatter from the detected x-rays using interpolation.

41. The system of claim 28, wherein the x-ray measuring device is further configured to use a dual-energy decomposition and/or linear method for decomposition to produce the at least one image and/or to identify the at least one substance.

42. The system of claim 28, wherein the x-ray source is configured to illuminate the subject with broad-spectrum x-rays and the x-ray measuring device is further configured to measure the received x-rays using energy-sensitive or photon-counting methods.

43. The system of claim 28, wherein the system is configured to identify and determine at least one of properties or characteristics of the substance by measurements using the x-ray measuring device and/or using simulated, synthesized, and/or predefined data.

44. The system of claim 43, wherein a quantitative relationship between a measurement of a known material and the substance to be measured relates to one or more of a density, atomic z, or a thickness of the respective material and substance where the known material and the substance have similar attenuation properties of x-rays.

45. The system of claim 28, wherein the database further comprises stored sinogram CT, CT, MM, SPECT, PET, spectroscopy, photoacoustic and other energy, chemical and/or electrochemical measurements.

* * * * *